US 7,764,986 B2

(12) United States Patent
Rice et al.

(10) Patent No.: US 7,764,986 B2
(45) Date of Patent: *Jul. 27, 2010

(54) METHOD AND APPARATUS FOR DETERMINING TARGET DEPTH, BRIGHTNESS AND SIZE WITHIN A BODY REGION

(75) Inventors: Bradley W. Rice, Danville, CA (US); Daniel G. Stearns, Mountain View, CA (US); Tamara L. Troy, San Francisco, CA (US)

(73) Assignee: Xenogen Corporation, Alameda, CA (US)

( * ) Notice: Subject to any disclaimer, the term of this patent is extended or adjusted under 35 U.S.C. 154(b) by 374 days.

This patent is subject to a terminal disclaimer.

(21) Appl. No.: 11/829,930

(22) Filed: Jul. 29, 2007

(65) Prior Publication Data

US 2007/0270697 A1    Nov. 22, 2007

Related U.S. Application Data

(63) Continuation of application No. 10/151,463, filed on May 17, 2002, now Pat. No. 7,403,812.

(60) Provisional application No. 60/291,794, filed on May 17, 2001.

(51) Int. Cl.
*A61B 6/00* (2006.01)

(52) U.S. Cl. .................. 600/473; 600/476; 600/431; 424/9.6

(58) Field of Classification Search ......... 600/473–476, 600/431, 410, 310, 317; 424/9.1, 9.6; 356/317
See application file for complete search history.

(56) References Cited

U.S. PATENT DOCUMENTS 4,687,325 A    8/1987    Corby, Jr.

(Continued)

FOREIGN PATENT DOCUMENTS

EP    1 016 419    7/2000

(Continued)

OTHER PUBLICATIONS

Achilefu et al., "Novel Receptor-Targeted Fluorescent Contrast Agents for In Vivo Tumor Imaging", Investigative Radiology, vol. 35(8), Aug. 200, pp. 479-485.

(Continued)

*Primary Examiner*—Long V Le
*Assistant Examiner*—Sanjay Cattungal
(74) *Attorney, Agent, or Firm*—Beyer Law Group LLP

(57) ABSTRACT

A method of investigating the location and size of a light-emitting source in a subject is disclosed. In practicing the method, one first obtains a light intensity profile by measuring, from a first perspective with a photodetector device, photons which (i) originate from the light-emitting source, (ii) travel through turbid biological tissue of the subject, and (iii) are emitted from a first surface region of interest of the subject. The light-intensity profile is matched against with a parameter-based biophotonic function, to estimate function parameters such as depth and size. The parameters so determined are refined using data other than the first measured light intensity profile, to obtain an approximate depth and size of the source in the subject. Also disclosed is an apparatus for carrying out the method.

20 Claims, 14 Drawing Sheets

U.S. PATENT DOCUMENTS

| | | |
|---|---|---|
| 4,687,352 A | 8/1987 | Igi et al. |
| 4,773,097 A | 9/1988 | Suzaki et al. |
| 5,202,091 A | 4/1993 | Lisenbee |
| 5,205,291 A | 4/1993 | Potter |
| 5,242,441 A | 9/1993 | Avitall |
| 5,319,209 A | 6/1994 | Miyakawa et al. |
| 5,334,193 A | 8/1994 | Nardella |
| 5,414,258 A | 5/1995 | Liang |
| 5,452,723 A | 9/1995 | Wu et al. |
| 5,584,872 A | 12/1996 | LaFontaine et al. |
| 5,594,253 A | 1/1997 | Bueno et al. |
| 5,636,299 A | 6/1997 | Bueno et al. |
| 5,637,874 A | 6/1997 | Honzawa et al. |
| 5,650,135 A | 7/1997 | Contag et al. |
| 5,661,562 A | 8/1997 | Aharon |
| 5,672,881 A | 9/1997 | Striepeke et al. |
| 5,705,807 A | 1/1998 | Throngnumchai |
| 5,738,101 A | 4/1998 | Sappey |
| 5,746,210 A | 5/1998 | Benaron et al. |
| 5,807,262 A | 9/1998 | Papaioannou et al. |
| 5,812,310 A | 9/1998 | Stewart et al. |
| 5,818,587 A | 10/1998 | Devaraj et al. |
| 5,835,617 A | 11/1998 | Ohta et al. |
| 5,840,572 A | 11/1998 | Copeland |
| 5,865,754 A | 2/1999 | Sevick-Muraca et al. |
| 5,867,250 A | 2/1999 | Baron |
| 5,917,190 A | 6/1999 | Yodh et al. |
| 5,943,129 A | 8/1999 | Hoyt et al. |
| 5,953,446 A | 9/1999 | Opsal et al. |
| 5,963,658 A | 10/1999 | Klibanov et al. |
| 5,970,164 A | 10/1999 | Bamberger |
| 6,069,698 A | 5/2000 | Ozawa et al. |
| 6,108,576 A | 8/2000 | Alfano et al. |
| 6,175,407 B1 | 1/2001 | Sartor |
| 6,205,347 B1 | 3/2001 | Morgan et al. |
| 6,208,886 B1 | 3/2001 | Alfano et al. |
| 6,217,847 B1 | 4/2001 | Contag et al. |
| 6,219,566 B1 | 4/2001 | Weersink et al. |
| 6,242,743 B1 | 6/2001 | DeVito et al. |
| 6,252,623 B1 | 6/2001 | Lu et al. |
| 6,264,610 B1 | 7/2001 | Zhu |
| 6,267,477 B1 | 7/2001 | Karpol et al. |
| 6,321,111 B1 | 11/2001 | Perelman et al. |
| 6,332,087 B1 | 12/2001 | Svenson et al. |
| 6,364,829 B1 | 4/2002 | Fulghum |
| 6,373,557 B1 | 4/2002 | Mengel et al. |
| 6,373,568 B1 | 4/2002 | Miller et al. |
| 6,377,353 B1 | 4/2002 | Ellis |
| 6,381,302 B1 | 4/2002 | Berestov |
| 6,392,241 B1 | 5/2002 | Rushbrooke et al. |
| 6,394,965 B1 | 5/2002 | Klein |
| 6,403,947 B1 | 6/2002 | Hoyt et al. |
| 6,415,051 B1 | 7/2002 | Callari et al. |
| 6,429,943 B1 | 8/2002 | Opsal et al. |
| 6,529,627 B1 | 3/2003 | Callari et al. |
| 6,549,288 B1 | 4/2003 | Migdal et al. |
| 6,597,931 B1 | 7/2003 | Cheng et al. |
| 6,615,061 B1 | 9/2003 | Khalil et al. |
| 6,615,063 B1 | 9/2003 | Ntziachristos |
| 6,618,152 B2 | 9/2003 | Toida |
| 6,618,463 B1 | 9/2003 | Schotland et al. |
| 6,628,401 B2 | 9/2003 | Toida |
| 6,628,747 B1 | 9/2003 | Schotland et al. |
| 6,636,755 B2 | 10/2003 | Toida |
| 6,642,953 B1 | 11/2003 | Nieto Velasco et al. |
| 6,646,678 B1 | 11/2003 | Kobayashi |
| 6,665,072 B2 | 12/2003 | Hoyt |
| 6,690,466 B2 | 2/2004 | Miller et al. |
| 6,690,520 B1 | 2/2004 | Kusuzawa |
| 6,693,710 B1 | 2/2004 | Hoyt |
| 6,710,770 B2 | 3/2004 | Tomasi et al. |
| 6,750,964 B2 | 6/2004 | Levenson et al. |
| 6,775,349 B2 | 8/2004 | Schotland et al. |
| 6,775,567 B2 | 8/2004 | Cable |
| 6,813,030 B2 | 11/2004 | Tanno |
| 6,919,919 B2 | 7/2005 | Nelson et al. |
| 6,924,893 B2 | 8/2005 | Oldenbourg et al. |
| 6,963,375 B1 | 11/2005 | Lundberg |
| 7,113,217 B2 | 9/2006 | Nilson et al. |
| 7,184,047 B1 | 2/2007 | Crampton |
| 7,263,157 B2 | 8/2007 | Bruder et al. |
| 2002/0001080 A1 | 1/2002 | Miller |
| 2003/0002028 A1 | 1/2003 | Rice et al. |
| 2003/0099329 A1 | 5/2003 | Schotland et al. |
| 2004/0010192 A1 | 1/2004 | Benaron et al. |
| 2004/0015062 A1 | 1/2004 | Ntziachristos et al. |
| 2004/0021771 A1 | 2/2004 | Stearns et al. |
| 2004/0027659 A1 | 2/2004 | Messerschmidt et al. |
| 2004/0085536 A1 | 5/2004 | Schotland et al. |
| 2004/0262520 A1 | 12/2004 | Schotland et al. |
| 2005/0149877 A1 | 7/2005 | Rice et al. |
| 2005/0283071 A1 | 12/2005 | Ripoll et al. |
| 2006/0118742 A1 | 6/2006 | Levenson et al. |
| 2006/0119865 A1 | 6/2006 | Hoyt et al. |
| 2006/0146346 A1 | 7/2006 | Hoyt |
| 2006/0173354 A1 | 8/2006 | Ntziachristos et al. |
| 2006/0203244 A1 | 9/2006 | Nilson et al. |
| 2006/0245631 A1 | 11/2006 | Levenson |
| 2006/0268153 A1 | 11/2006 | Rice et al. |
| 2007/0016078 A1 | 1/2007 | Hoyt et al. |

FOREIGN PATENT DOCUMENTS

| | | |
|---|---|---|
| JP | 06-129984 | 5/1994 |
| JP | 08-136448 | 5/1996 |
| JP | 11-173976 | 7/1999 |
| WO | 96/16596 | 6/1996 |
| WO | WO97/40381 | 10/1997 |
| WO | WO98/34533 | 8/1998 |
| WO | WO 00/17643 | 3/2000 |
| WO | WO00/36106 | 6/2000 |
| WO | WO00/54581 | 9/2000 |
| WO | WO01/18225 | 3/2001 |
| WO | WO01/63247 | 8/2001 |
| WO | WO02/41760 | 5/2002 |

OTHER PUBLICATIONS

Arridge, "Photon-Measurement Density Functions. Part 1: Analytical Forms", Applied Optics, vol. 34, No. 31, Nov. 1, 1995, pp. 7395-7409.

Arridge, "Photon-Measurement Density Functions. Part 2: Finite-Element-Method Calculations", Applied Optics, vol. 34, No. 34, Dec. 1, 1995, pp. 8026-8037.

Australian Office Action dated Jul. 25, 2006 for Australian Application No. 2002303819.

Becker et al., "receptor-Targeted Optical Imaging of Tumors with Near-Infrared Fluorescent Ligands", Nature Biotechnology, vol. 19, Apr. 2001, pp. 327-330.

Benaron, David A., "A System for Imaging Infection and Gene Expression in the Body in 3-D," Biomedical Optical Spectroscopy and Diagnostics, 1998 Technical Digest, 1998, Optical Society of America, pp. 134-135.

Bevilacqua et al., "In Vivo Local Determination of Tissue Optical Properties: Applications to Human Brain", Applied Optics, vol. 38, No. 22, Aug. 1, 1999, pp. 4939-4950.

Bevilacqua et al., "Monte Carlo Study of Diffuse Reflectance at Source-Detector Separations Close to One Transport Mean Free Path", Optical Society of America, vol. 16, No. 12, Dec. 1999, pp. 2935-2945.

Bouvet et al., "Real-Time Optical Imaging of Primary Tumor Growth and Multiple Metastatic Events in a Pancreatic Cancer Orthotopic Model", Cancer Research, vol. 62, Mar. 1, 2002, pp. 1534-1540.

Chang et al., "Improved Reconstruction Algorithm for Luminescence Optical Tomography When Background Lumiphore is Present", Applied Optics, vol. 37, No. 16, Jun. 1, 1998, pp. 3547-3552.

Cheong et al., "A review of the Optical Properties of Biological Tissues", IEEE Journal of Quantum Electronics, vol. 26, No. 12, Dec. 1990, pp. 2166-2185.

Contag et al., "Photonic Detection of Bacterial Pathogens in Living Hosts", Molecular Microbiology, vol. 18, No. 4, 1995, pp. 593-603.

Contag et al., "Use of Reporter Genes for Optical Measurements of Neoplastic Disease In Vivo", Neoplasia, vol. 2, Nos. 1-2, Jan.-Apr. 2000, pp. 41-52.

EP Search Report dated Oct. 6, 2006 for EP Application No. EP 06 01 3492.

Eppstein et al., "Biomedical Optical Tomography Using Dynamic Parameterization and Bayesian Conditioning on Photon Migration Measurements", Applied Optics, vol. 38, No. 10, Apr. 1, 1999, pp. 2138-2150.

Francis et al, "Visualizing Pneumococcal Infections in the Lungs of Live Mice Using Bioluminescent Streptococcus Pneumoniae Transformed with a Novel Gram-Positive lux Transponson", Infection and Immunity, vol. 69, No. 5, pp. 3350-3358.

Frohn, "Super-Resolution Fluorescence Microscopy by Structured Light Illumination," Dissertation submitted to the Swiss Federal Institute of Technology, Zurich, 2000.

Ghiglia et al., "Two-Dimensional Phase Unwrapping: Theory, Algorithms, and Software", Wiley-Interscience publication, 1998, ISBN 0-471-24935-1, p. 312.

Haskell et al., "Boundary Condition for the Diffusion Equation in Radiative Transfer", Optical Society of America, vol. 11, No. 10, Oct. 1994, pp. 2727-2741.

Hastings, "Chemistries and Colors of Bioluminescent Reactions: a Review", Gene, vol. 173, 1996, pp. 5-11.

Hawrysz et al., "Developments Toward Diagnostic Breast Cancer Imaging Using Near-Infrared Optical Measurements and Fluorescent Contrast Agents", Neoplasia, vol. 2, No. 5 Sep.-Oct. 2000, pp. 388-417.

Ishimaru, "Wave Propagation and Scattering in Random Media", vol. 1, Single Scattering and Transport Theory, Academic Press, 1978.

Ishimaru, "Wave Propagation and Scattering in Random Media", vol. 2, Multiple Scattering Turbulence Rough Surfaces and Remote Sensing, Academic Press, 1978.

Kienle, "Noninvasive Determination of the Optical Properties of Two-Layered Turbid Media", Applied Optics, vol. 37, No. 4, Feb. 1, 1998, pp. 779-791.

Mahmood et al., "Near-Infrared Optical Imaging of Protease Activity for Tumor Detection", Radiology, Dec. 1999, p. 866-870.

Maston (editor), "Biological Techniques: Fluorescent and Luminescent Probes for Biological Activity: A Practical Guide to Technology for Quantitative Real-Time Analysis", Second Edition, Academic Press, 1999.

Ntziachristos et al., "Experimental Three-Dimensional Fluorescence Reconstruction of Diffuse Media by Use of a Normalized Born Approximation", Optical Society of America, vol. 26, No. 12, Jun. 15, 2001, pp. 893-895.

Ntziachristos et al., "Fluorescence Molecular Tomography Resolves Protease Activity In Vivo", Nature Medicine, vol. 8, No. 7, Jul. 2002, pp. 757-760.

Office Action received in EP Application No. 03764754.2 dated Feb. 7, 2007.

Pickering et al., "Double-integrating-sphere system for measuring the optical properties of tissue," Applied Optics, Feb. 1, 1993, vol. 32, No. 4, pp. 399-410.

Prahl et al., "Determining the Optical Properties of Turbid Media by Using the Adding-Doubling Method", Applied Optics, vol. 32, No. 4, Feb. 1, 1993, pp. 559-568.

Rehemtulla et al., "Rapid and Quantitative Assessment of Cancer Treatment Response Using In Vivo Bioluminescence Imaging", Neoplasia, vol. 2, No. 6, 2000, pp. 491-495.

Research & Development (magazine), vol. 42, No. 9, Sep. 2000, Part 1 of 2.

Rice et al., "Advances in 2D In Vivo Optical Imaging Instrumentation," Abstract No. 186, Society for Molecular Imaging $2^{nd}$ Annual Meeting, Aug. 2003.

Rice et al., "In Vivo Imaging of Light-Emitting Probes", Journal of Biomedical Optics, vol. 6, No. 4, Oct. 2001, pp. 432-440.

Takeda et al., "Fourier-Transform Method of Fringe-Pattern Analysis for Computer-Based Topography and Interferometry", Optical Society of America, vol. 72, No. 1, Jan. 1982, pp. 156-160.

Toyooka et al., "Automatic Profilometry of 3-D Diffuse Objects by Spatial Phase Detection", Applied Optics, vol. 25, No. 10, May 15, 1986, p. 1630-1633.

Tromberg et al., "Properties of Photon Density Waves in Multiple-Scattering Media", Applied Optics, vol. 32, No. 4, Feb. 1, 1993, p. 607-616.

Tuchin, "Tissue Optics: Light Scattering Methods and Instruments for Medical Diagnosis", SPIE Press, 2000.

Weissleder et al., "In Vivo Imaging of Tumors with Protease-Activated Near-Infrared Fluorescent Probes", Nature Biotechnology, vol. 17, Apr. 1999, pp. 375-378.

Weissleder et al., "Shedding Light onto Live Molecular Targets", Nature Medicine, vol. 9, No. 1, Jan. 2003, p. 123-1218.

Windsor et al., "Imaging Pulmonary Inflammation Using Fluorescence Molecular Tomography," Society for Molecular Imaging, Sep. 23, 2005.

Wu et al., "Noninvasive Optical Imaging of Firefly Luciferase Reporter Gene Expression in Skeletal Muscles of Living Mice", Molecular Therapy, vol. 4, No. 4, Oct. 2001, pp. 297-306.

Yang et al., "Whole-Body Optical Imaging of Green Fluorescent Protein-Expressing Tumors and Metastases", PNAS, vol. 97, No. 3, Feb. 1, 2000, pp. 1206-1211.

Zhang et al., "Rapid In Vivo Functional Analysis of Transgenes in Mice Using Whole Body Imaging of Luciferase Expression", Transgenic Research, vol. 10, 2001, pp. 423-434.

European Office Action dated Aug. 21, 2008 from EP Patent Application No. 03764754.2.

International Search Report dated Jul. 7, 2008 from PCT Application No. PCT/US08/59492.

Written Opinion dated Jul. 7, 2008 from PCT Application No. PCT/US08/59492.

Ntziachristos, Fluorescence Molecular Imaging, Annual Reviews of Biomedical Engineering, Aug. 2006, vol. 8, pp. 1-33.

Office Action dated Aug. 4, 2008 from U.S. Appl. No. 10/606,976.

Tauler et al., "Multivariate Curve Resolution Applied to Spectral Data from Multiple Runs of an Industrial Process," Analytical Chemistry, vol. 65, No. 15, Aug. 1, 1993, pp. 2040-2047.

Jaumot et al., "A graphical user-friendly interface for MCR-ALS: a new tool for multivariate curve resolution in MATLAB," Chemometrics and Intelligent Laboratory Systems 76, 2005, pp. 101-110.

Wentzell et al., "Multivariate curve resolution of time course microarray data," BMC Bioinformatics 2006, 7:343, submitted Mar. 18, 2006, published Jul. 13, 2006.

Duponchel et al., "Multivariate curve resolution methods in imaging spectroscopy: influence of extraction methods and instrumental perturbations," J. Chem. Inf. Comput. Sci., vol. 43, No. 6, 2003, pp. 2057-2067.

Notice of Allowance dated Mar. 19, 2008 from U.S. Appl. No. 10/151,463.

European Examination Report dated Apr. 8, 2008 from EP Patent Application No. 06013492.1.

Chinese Office Action dated Apr. 4, 2008 from Chinese Patent Application No. 03821121.1.

Office Action dated Jun. 9, 2008 from Japanese Patent Application No. 2002-589773.

Office Action dated Aug. 6, 2008 from U.S. Patent Appl. No. 11/733,358.

Notice of Allowance dated Sep. 16, 2009 in U.S. Appl. No. 10/606,976.

Office Action dated May 7, 2009 in U.S. Appl. No. 10/606,976.

Office Action dated Apr. 16, 2009 in U.S. Appl. No. 11/829,919.

Notice of Allowance dated Mar. 23, 2009 in U.S. Appl. No. 11/829,927.

Office Action dated Dec. 10, 2008 in U.S. Appl. No. 10/606,976.

Mouaddib et al., "Recent Progress in Structured Light in Order to Solve the Correspondence Problem in Stereo Vision", International Conference of Robotics and Automation, Albuquerque, New Mexico, Apr. 1997 pp. 130-136.

Battle et al., "Recent Progress in Coded Structured Light as a Technique to Solve the Correspondence Problem: A Survey", Pattern Recognition, vol. 31, No. 7, 1998, pp. 963-982.

Fofi et al., "Uncalibrated Vision Based on Structured Light", Proceedings of the 2001 IEEE International Conference on Robotics and Automation, Seoul, Korea, May 2001, pp. 3548-3553.

Scharstein et al., "High-Accuracy Stereo Depth Maps Using Structured Light", IEEE Computer Society Conference on Computer Vision and Pattern Recognition (CVPR) 2003), vol. 1, Madison, Wisconsin, pp. 195-202.

Notice of Allowance dated Aug. 24, 2009 in U.S. Appl. No. 11/829,919.

Office Action dated Nov. 17, 2009 in U.S. Appl. No. 11/127,346.

Summons to attend oral proceedings dated Sep. 28, 2009 for European Application No. 03764754.2.

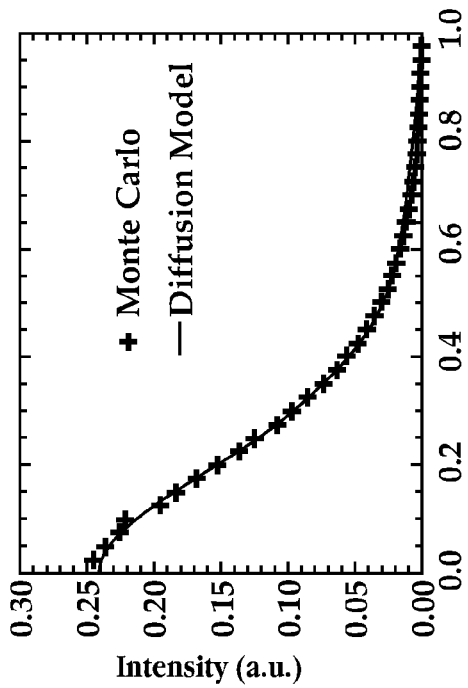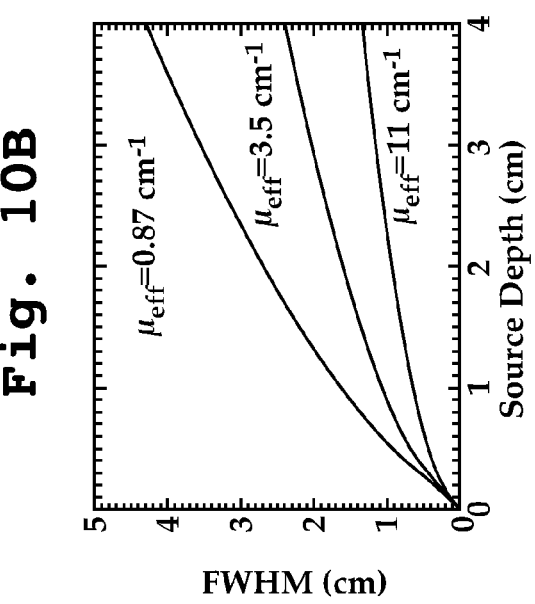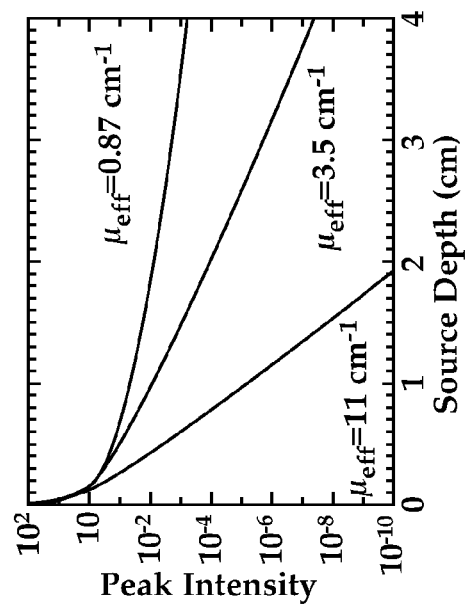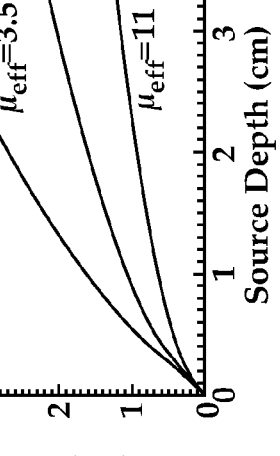
Fig. 10A
Fig. 10B
Fig. 11A
Fig. 11B

METHOD AND APPARATUS FOR DETERMINING TARGET DEPTH, BRIGHTNESS AND SIZE WITHIN A BODY REGION

CROSS REFERENCE TO RELATED APPLICATIONS

This application is a continuation of U.S. patent application Ser. No. 10/151,463, filed May 17, 2002 and entitled, "METHOD AND APPARATUS FOR DETERMINING TARGET DEPTH, BRIGHTNESS AND SIZE WITHIN A BODY REGION", which claims priority to Provisional Application Ser. No. 60/291,794 filed on May 17, 2001; each of these patent applications is incorporated by reference herein in its entirety for all purposes.

FIELD OF THE INVENTION

This invention relates to an apparatus and method for fields of non-invasive medical imaging, medical research, pathology, and drug discovery and development.

BACKGROUND

In a variety of medical diagnostic and therapeutic settings, as well as in biomedical research, it is desirable to image a subsurface target or area within a body region of a subject. For example, non-invasive locating and imaging of part or all of a solid tumor, an area of myocardial ischemia, the distribution of a therapeutic compound administered to the subject, or the progression of a disease may provide useful research or diagnostic information. Ideally, an imaging method is able to locate within a body region a target of interest, and provide information about the target's shape, size, number of cells, and depth below the surface of the body region. However, until now, methods that have been used and/or proposed for subsurface body target imaging have generally been limited to those using ionizing radiation such as X-rays, expensive and bulky equipment such as Magnetic Resonance imaging (MRI), or ultra-sound.

X-rays have excellent tissue penetration, and when used in conjunction with computed tomography (CT) or computed axial tomography (CAT), can produce superior image quality. However, X-rays have limited use in monitoring disease progress because exposure to X-rays is potentially harmful if such exposure is prolonged. X-rays can be used to locate and image compositions that have localized at a target within a body region, but always with exposure to the potential harm associated with X-ray radiation. X-rays, however, cannot readily be used to image the expression of gene products in vivo and determine the depth and/or shape of a target expressing such gene products.

MRI is also an excellent method for imaging targets, areas, and structures in a body region of a subject. Although MRI is not thought to possess harmful attributes like those associated with ionizing radiation, the expense and bulky equipment size needed to use MRI make it impractical for many applications or situations. MRI can provide two and three-dimensional information about targets within a body region of a subject, but is less effective at imaging physiological activity associated with a target.

Ultrasound or ultrasonography is the use of high-frequency sound (ultrasonic) waves to produce images of structures within the human body. Ultrasonic waves are sound waves that are above the range of sound audible to humans. Ultrasonic waves are produced by the electrical stimulation of a piezoelectric crystal and such waves can be aimed at specific body regions. As the waves travel through body tissues within a body region, they are reflected back at any point where there is a change in tissue density, as, for instance, in the border between two different organs of the body. Ultrasound offers the advantages of not using radiation or radioactive material, and employs lesser expensive and less bulky equipment than MRI, but is limited to only discerning differences in density of underlying tissue and structures. Accordingly, ultrasound cannot effectively track and monitor the progress of an infection unless such infection results in a discernable shift in density of the target tissue. Ultrasound cannot image or detect the physiological functions of tissues or organs.

Until now, Positron Emission Tomography or P.E.T. was unique among imaging techniques because it produces an image of organ or tissue function. Other imaging techniques such as X-ray, CT, MRI, and sonography depict organ or tissue anatomy but cannot discern physiological activity within them. To image a specific biochemical activity of an organ, a radioactive substance, called a radiotracer or radiopharmaceutical, is injected into the body or inhaled. The tracer is usually a radioactive equivalent of a substance that occurs naturally within the body such as water or sugar. The radioactive isotope is identical to the body's own nonradioactive isotope except that its atoms have a different number of neutrons. Consequently, a subject's body is burdened with radioactive material, and the potential harm associated with such material. P.E.T cannot detect non-isotopic expression products from transgenic tissues, organs, or transgenic organisms. Scintigraphy, a diagnostic technique in which a two-dimensional picture of a bodily radiation source is obtained by the use of radioisotopes, may also be used for imaging structures and their functions. Scintigraphy, however, is not suitable for determining the depth of a target in a body region of a subject.

In view of the above-mentioned technologies for locating and imaging a target in a body region of a subject, there is a need for methods and devices to determine the depth and/or the shape and/or number of cells of such target without having to use radioactivity, radiation, or expensive and bulky equipment. The invention disclosed herein meets these needs.

SUMMARY

In one aspect, the invention includes a method of investigating the location, size and number of cells, of a light-emitting source in a subject. In practicing the method, one initially obtains a first measured light intensity profile constructed by measuring, from a first perspective with a photodetector device, photons which (i) originate from the light-emitting source, (ii) travel through turbid biological tissue of the subject, and (iii) are emitted from a first surface region of interest of the subject. The light-intensity profile is matched against a parameter-based biophotonic function to estimate function parameters such as depth and size. The parameters so determined are refined using data other than the first measured light intensity profile, to obtain an approximate depth and size of the source in the subject. The additional data may be data measured from the subject, data from modeling analysis, or data relating to the wavelength of photons emitted from the surface of the subject. As examples:

The method typically includes generating a 2-D or 3-D visual representation of the light-emitting source, using the approximate depth and shape of the source in the subject, and superimposing the visual representation onto a 2-D or 3-D image of the subject.

The additional data may be obtained from computer simulation of the diffusion of light from a light-emitting source in a turbid medium. One preferred simulation approach involves (i) generating a plurality of theoretical light-intensity profiles, based on a model of photon diffusion from a glowing source located at one of a plurality of depths, and having one of a plurality of sizes and shapes, through a turbid medium having absorption and scattering properties similar to those of biological tissue, (ii) comparing the quality of fit between each of the plurality of theoretical light-intensity profiles and the first measured light intensity profile, (iii) selecting the theoretical light intensity profile which provides to the first measured light intensity profile, and (iv) obtaining an approximate depth, shape and brightness of the source in the subject using parameters from the theoretical light intensity profile selected in (iii). The method may include employing in a photon-scattering model, one or more predetermined tissue-specific light-scattering coefficients corresponding to tissue through which the photons travel.

In another general embodiment, the additional data are obtained by measuring light emission from the subject at two or more different wavelengths between about 400 nm and about 1000 nm, determining the relative light intensities measured at the different wavelengths, and comparing the determined relative light intensities with known relative signal intensities at the different wavelengths, as a function of tissue depth. Alternatively, the spectrum of light intensities is measured over a selected wavelength range between about 400-1000 nm, and the measured spectrum is compared with a plurality of spectra measured from light-emitting sources placed at various depths within tissue, to determine the depth of the light-emitting source from matching the measured spectrum with the known spectra.

In various embodiments for a light-emission source, the source is a luminescent moiety or a fluorescent moiety; the light-emitting source is administered to the subject and binds to a selected target or is otherwise localized in the subject prior to the measuring; and the light-emitting source is a light-generating protein (e.g., a luciferase, a green fluorescent protein, etc.), such as a light-generating protein expressed by biological cells of the subject or biological cells administered to the subject.

In another aspect, the invention includes apparatus for use in investigating the location and size of a light-emitting source in a subject. The apparatus includes a light-tight enclosure within which light-emission events from the subject can be detected and an optical system associated with the enclosure for use in generating a first light intensity profile constructed by measuring, from a first perspective within the enclosure, photons which (i) originate from the light-emitting source, (ii) travel through turbid biological tissue of the subject, and (iii) are emitted from a first surface region of interest of the subject. A computational unit operatively connected to the photo-detector functions to (i) fit the first measured light intensity profile with a parameter-based biophotonic function; and (ii) refine the parameters of the biophotonic function, using data other than the first measured light intensity profile, to generate an approximate depth and shape of the source in the subject.

The optical system preferably includes an intensified or cooled charge-coupled-device (CCD), and a lens for focusing light onto the CCD. The optical system may configured in such a way as to detect photons emitted from a plurality of different selected surface regions of interest of the subject. The system may include one or more filters for transmitting photons within different selected wavelength ranges, e.g., above and below 600 nm.

The computational unit may include a data file of model biophotonic functions representing light-emitting sources of various sizes at various depths, for curve matching with the first spatial profile.

Where the optical system includes filters for wavelength discrimination, the computation unit is operable to carry out at least one of the parameter-refinement operations:
 (i) determining the relative light intensities measured at the different wavelengths, and comparing the determined relative light intensities with known or calculated relative signal intensities at the different wavelengths, as a function of tissue depth; and
 (ii) comparing the measured spectrum with a plurality of spectra measured from light-emitting sources placed at various depths within tissue, and determining the depth of the light-emitting source from matching the measured spectrum with the known spectra.

In another embodiment, the computational unit is operable to average the intensity pattern image into a single intensity value, and further to determine source size by integrated light intensity values generated as a function of a light-emitting source of a particular size and shape.

The computational unit may have a database containing a plurality of theoretical light-intensity profiles, based on a model of photon diffusion from a light-emitting source located at one of a plurality of depths, and having one of a plurality of sizes and shapes, through a turbid medium having absorption and scattering properties similar to those of biological tissue. Here the computational unit is operable to (i) compare the quality of fit between each of the plurality of theoretical light-intensity profiles and first measured light intensity profile, (ii) select the theoretical light intensity profile which provides the best fit to the first measured light intensity profile, and (iii) obtain an approximate depth and shape of the source in the subject using parameters from the theoretical light intensity profile selected in (ii).

In addition, the computational unit is operable to generate a visual 2-, or 3-dimensional representation of the light-emitting source, using the approximate depth and shape of the source in the subject, and superimposing the visual representation onto a 2- or 3-dimensional image of the subject.

In another aspect, the invention provides a method of determining the depth of a light-emitting source in a subject. In practicing the method, the light emission intensity from the subject at two or more different wavelengths between about 400 and about 1000 nm is measured. The depth of the light-emitting source is determined using the measured light intensities and information related to the optical properties of the subject's tissue, e.g., coefficients of attenuation and diffusion in the subject.

Information relating to optical properties, e.g., the coefficients of attenuation and diffusion in the subject, may be obtained by direct measurement of the coefficients in material that is the same or similar to that of the subject.

Alternatively, optical-properties information may be obtained indirectly, by determining, at two or more different wavelengths, light intensities from a light-emitting source located at each of a plurality of depths in tissue or material corresponding to that of the subject. The desired depth determination is then carried out by matching the measured light intensities with the light intensities determined at each of the plurality of depths.

In the latter approach, the spectral profile of light intensities from the light-emitting source may be compared (matched) with each of a plurality of spectral profiles of light intensities from a light-emitting source at each of a plurality of depths.

BRIEF DESCRIPTION OF THE DRAWINGS

FIG. 10A shows a Monte Carlo simulation following a photon through a "random walk" through turbid tissue.

FIG. 10B illustrates a calculated light intensity spatial profile calculated for a light source at 4 mm depth from the diffusion model (solid line) and with Monte Carlo simulations ("+" symbols).

FIGS. 11A and 11B are plots calculated from the diffusion model showing peak intensity (11A) and spot width (FWHM) (10B) as a function of source depth.

DETAILED DESCRIPTION OF THE INVENTION

I. Definitions

Figure 1A:
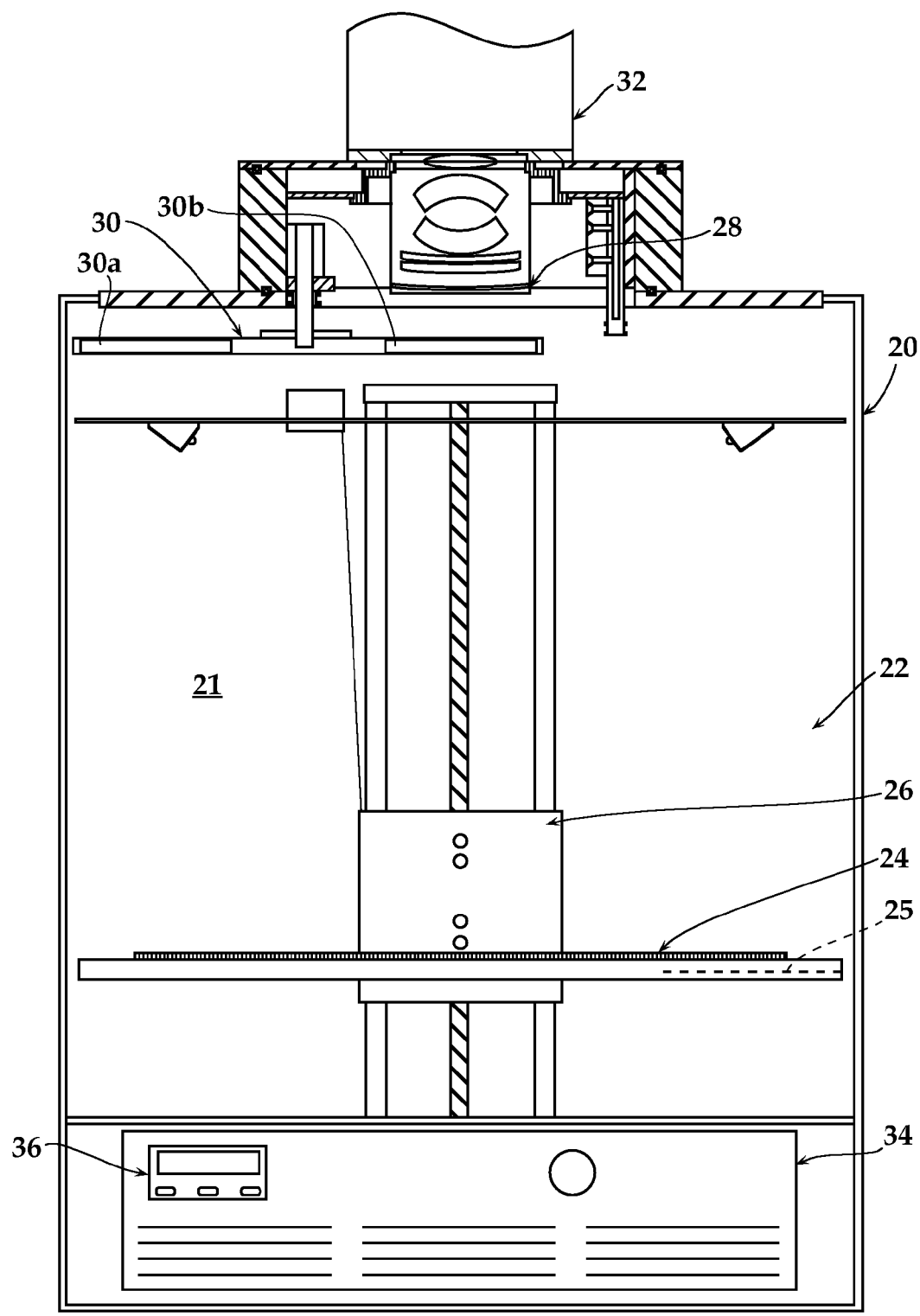
FIG. 1A is a cross-sectional view of an apparatus constructed in accordance with the invention, for use in investigating the location and size of a light-emitting source in a subject.

Unless otherwise indicated, the terms below are defined as follows:

A "biophotonic function" is a mathematical function that describes a measurable photonic output, such as a light emission profile, spectral intensity distribution, or integrated light intensity, in terms of photonic-source variables, such as source depth, size and shape, number of light-emitting cells, wavelength-dependent scattering and absorption coefficients for specific types of tissue, and spectral characteristics of the light-emitter. The photonic function can be based, for example, on a photon-diffusion model, as discussed below, on a Monte-Carlo simulation, or finite element analysis.

"Turbid tissue" is non-transparent tissue in a subject that has both light scattering and light absorption properties.

"Target region" refers to an internal subsurface region in a subject, such as a subsurface tissue or organ, a solid tumor, or a region of infection, that is (i) localized within the subject, (ii) separated from the surface region of the subject by turbid tissue, and (iii) preferably possesses at least one distinguishable feature, such as a tissue or organ-specific antigen, gene or gene product, either as mRNA or expressed protein, a product resulting from activation, deactivation, or regulation, of a cell, organ, or tissue.

Light-emitting source refers to a source of light emission at the target region. The source may itself emit visible light, such as when the target tissue is genetically modified to produce recombinant light-emitting protein when specific genes are expressed by some activation means. In preferred embodiments, different types of light-generating proteins, such as bioluminescent proteins (e.g., luciferases) and fluorescent proteins (e.g., GFP, dsRed, and YFP) are employed. Exemplary light-emitting sources include prokaryotic and eukaryotic cells transformed with a light-generating protein and administered to the animal subject, as well as light-producing cells which are intrinsically part of an animal made transgenic for a light-generating reporter gene.

Alternatively, the source may include fluorescent or other molecules that can be excited by electromagnetic radiation to emit visible light. For example, a composition effective to cause a target to emit light may be administered to the subject and allowed to localize at the target location wherein the composition will then emit light, or cause some other moiety in or adjacent the target to emit light. For example, the administered composition may be a compound which activates cells in or adjacent the target, and in-turn, causes such cells to emit light, hence, the localized cells are the target within the subject's body region. In yet other embodiments, infectious cells are administered to a subject, and the progress and locality of the disease are determined. The target, in this embodiment, is the cluster of cells at a given point having a location within the body region of the subject. In other embodiments of the invention, a body region may have multiple targets, and a subject may have multiple body regions, each region potentially having a target.

"Fluorochromes" or "fluorophores" are molecules which are excited at or effectively near an excitation maxima, and emit or fluoresce light at longer wavelengths. The difference between the excitation maxima of a fluorochrome, and the emission maxima of the fluorochrome, is known as a Stokes shift. The greater the Stokes shift for a given fluorochrome, the greater the difference in between the excitation spectrum, or range of wavelengths, which excites the fluorochrome, and the emission spectrum or range of wavelengths of light emitted by the fluorochrome when is fluoresces. Certain embodiments of the invention employ fluorochromes with high Stokes shifts such with Texas Red, rhodamine, Cy3, Cy5, Cy7, and other deep, far red, or near infra-red (NIRF) fluorochromes. Particularly preferred fluorochromes emit light at wavelengths longer than about 600 nanometers. Other preferred fluorochromes will emit light in ranges shorter than 600 nanometers. In particular, variants of "green fluorescent protein" (GFP), each having various emission spectra, are particularly useful because, like luciferase, such proteins may be synthesized by the target or cells adjacent or associated with the target, or which localized at the target, for example, as in an infection. GFPs may further be administered as a conjugate to another protein or biological material that localizes at the target or targets.

In preferred embodiments of the invention, each light-emitting source, under known light-emitting conditions, has a known emission spectrum. Each emission spectrum is preferably constant throughout the detection step. In particular, the relative intensity of light emission at each wavelength of light remains relative to the intensity of light emission at all other wavelengths of light within the emission spectrum of the light-emitting source, as the overall intensity of the spectrum changes. Some embodiments of the invention minimally require at least two distinguishable ranges of wavelengths of emitted light. More preferably, particular embodiments of the invention require that each range of wavelengths of light behave differently, as a function of the distance or depth for which such light travels through the body region, from other ranges as they travel through a selected body region of a subject. For example, the intensity of a first range of wavelengths of light is cut in half for every centimeter of a body region the light travels, whereas a second range of wavelengths of light is cut by three fourth for every centimeter of body region the light travels through. The intensity of light having both ranges of wavelengths, where each range has the same intensity, will diminish by one half at the first range, and three quarters at the second range, after passing through one centimeter of tissue. By comparing the resulting 2:1 ratio of intensities from the initial 1:1 ratio of intensities at tissue depth zero, a determination that the light traveled one centimeter through the tissue can be made.

The invention may be practiced using different light-emitting sources such as different luciferase enzymes. For example, the light emission from "blue" bacterial luciferase (*Photorhabdus luminescens*) expressed on agar was analyzed by a spectrometer that revealed a spectrum centered about 485 nm. A "green" firefly luciferase (*Photinus pyralis*) expressed in PC-3M cells in PBS solution emitted light demonstrating a spectrum centered about 570 nm. A "red" luciferase expressed in PC-3M cells suspended in PBS solution demonstrated a spectrum centered about 620 nm.

II. Apparatus and Method

FIG. 1A is a cross-sectional view of an apparatus 20 which may be used in investigating the location and size of a light-emitting source in a subject, in accordance with the invention. The apparatus generally includes a light-tight enclosure or chamber 22 within which light-emission events from the subject can be detected. Light tight box 22 may be constructed as described in co-owned PCT publication number WO 200163247, which is herein incorporated by reference in its entirety. Briefly, the chamber is defined by back and side walls, such as back wall 21, and has a front opening (not shown, which can opened to provided access to the interior of the chamber, and closed to provide a light-tight seal. Although light tight box 22 was designed for small animals, the technology can also be applied to larger mammals, including humans.

Contained within the chamber is a stage 24 on which the subject is placed and preferably immobilized during light-emission detection. Although many of the examples described herein have to do with a small mammalian subject, typically a mouse or a rat, it will be appreciated that the same principles and methods will apply to other animals as well as human subjects, employing suitable scale-up in chamber size and where necessary, suitable increases in the size and number of light emitters in the target region. The stage in the apparatus shown is designed to be raised and lowered to a selected vertical position within the chamber by a conventional wormscrew mechanism shown generally at 26 and under user control. The stage position within the chamber may be monitored by any of a number of known tracking devices that do not require visible light signals.

The viewing optics includes to two general components. The first is a lens assembly 28 that serves to focus light-emission events from the surface of the subject onto the detection screen of a photodetector 32, which is typically a photodetector pixel array of a charged-coupled device that can be operated in a cooled condition to minimize intrinsic noise level. The construction of the lens assembly and its optical coupling to the detector is conventional. One preferred CCD is a model 620 CCD, commercially available from Spectral Instruments.

The second, and optional, component of the optical system is a wavelength filter wheel 30 containing a number of optical bandpass filters designed to block light transmission in all but a selected range of visible-light wavelengths. One standard installation includes 3 filters; a shortpass filter 30a, for wavelengths less than 510 nm (blue light filter), a midpass filter 30b having a bandpass in the 500-570 nm range (green light filter), and a longpass filter for wavelengths greater than 590 nm (red light filter). In some applications, filters can provide more precise bandpass, e.g., every 20 nm. The just-described viewing optics and detector are also referred to herein, collectively, as an optical system.

The apparatus also includes a control unit 34. Various user-controlled settings, such as stage height, orientation, and translation position, bandpass filter, and detector mode are made through a control input pane; 36 in the apparatus.

Figure 1B:
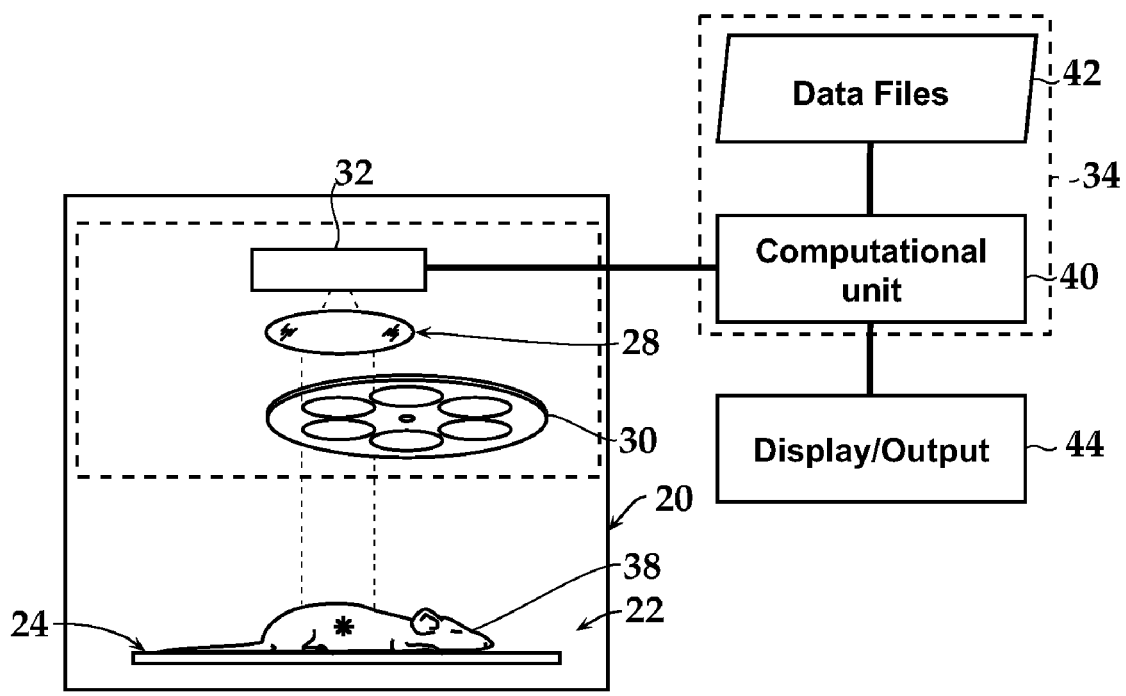
FIG. 1B illustrates features of the apparatus in FIG. 1A in schematic form.

FIG. 1B shows a more schematic representation of apparatus 20, here shown in a scale for use in imaging a small mammalian subject, such as a mouse 38. The lens assembly is represented here as a single lens 28, the filter wheel at 30, and a CCD detector at 32. The detector output is supplied to a computational unit 40 in the control unit computational unit 34 which includes a processor 40 and a storage unit 42 for data files. The content of the data files, and operation of the computational unit, in response to light-detection signals from the designs from detector 32 will be described below. The control unit is operatively connected to a display/output device 44, such as a computer monitor, for displaying information and images to the user.

The operation of the computational unit can be appreciated from the method of the invention carried out by the apparatus, which will be summarized with respect to FIG. 2, and detailed further below. The first step in the method is to obtain a first measured light-intensity profile. This is done by first localizing a light-emitting source within a subject. This may be done, as noted above, in a variety of ways, including introducing into the subject, a gene effective to produce a light-emitting protein, such as luciferase, in the target region, or localizing a fluorescent compound at the target source, both according to methods which are known, e.g., as described in co-owned PCT publications WO00/36106, WO01/18225, WO00/54581 and WO97/40381; all of which are incorporated herein by reference.

Figure 2:
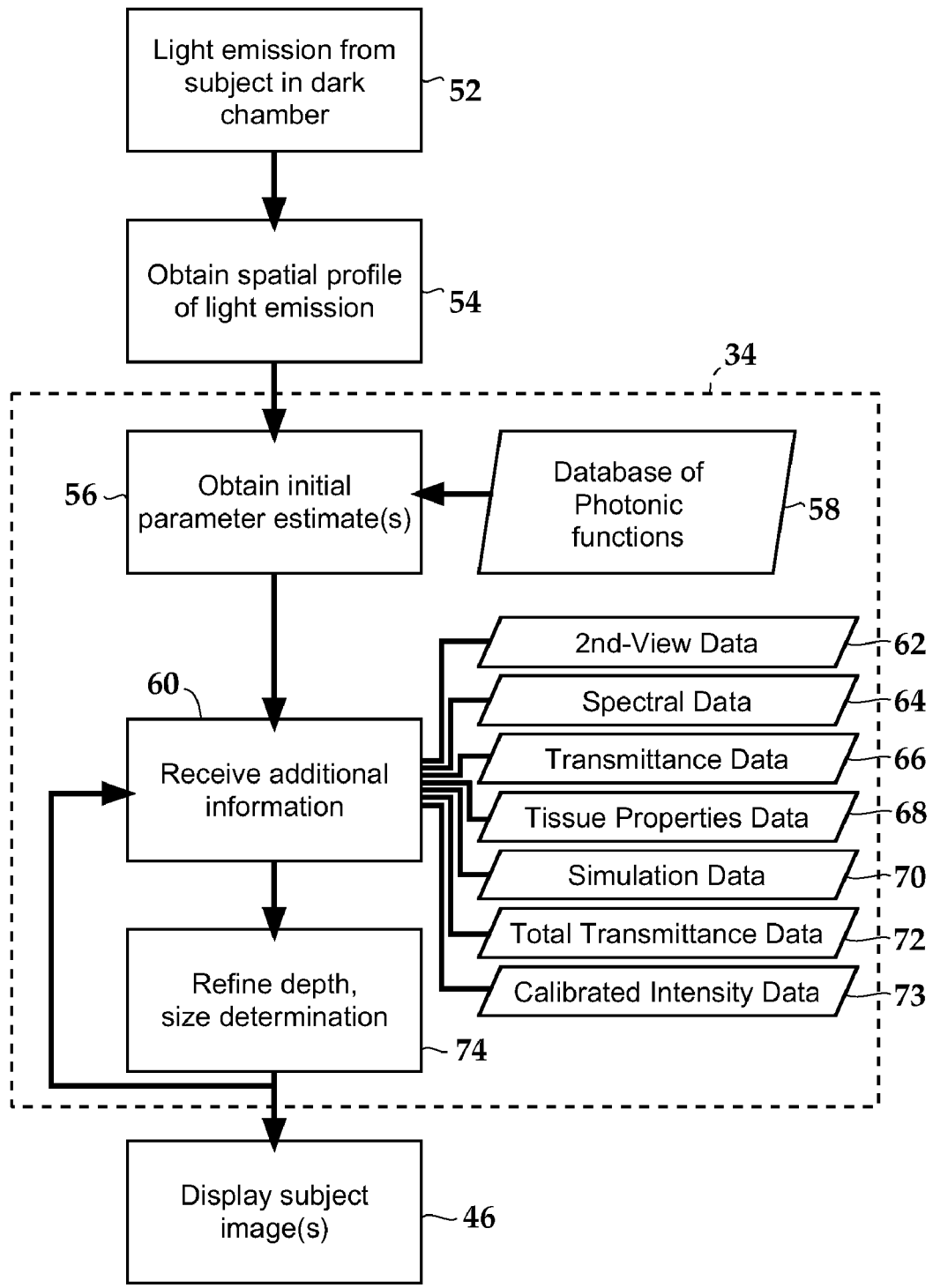
FIG. 2 is a flowchart of the general steps that can be carried out by the apparatus, in practicing the method of the invention.
Figure 3A:
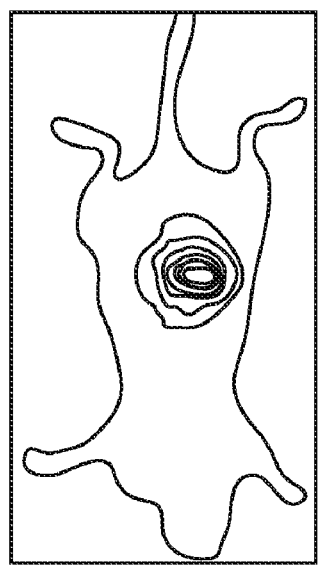
FIG. 3A is a surface light-intensity image from a light-emitting source in an animal subject.
Figure 3B:
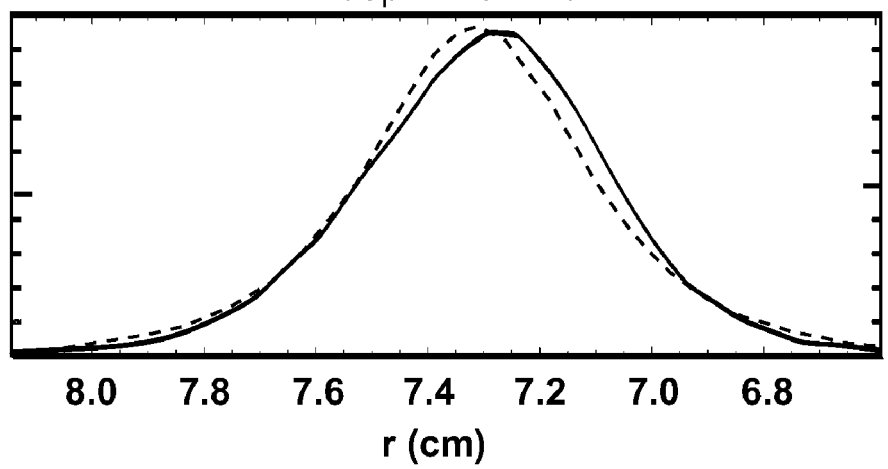
FIG. 3B is a light emission profile from the animal subject in FIG. 3A, showing the curve fit between the measured emission profile (solid lines) and a light-emission profile calculated from a diffusion model.

The subject so prepared is placed in the light-tight chamber, and light-emission form the subject surface originating from light-emission events at the target region are measured, digitized, and placed in the computational unit, as at 52 in FIG. 2. The computational unit uses this data to generate a spatial profile of light emission, as at 54. This profile could be taken along a selected row and a selected column of detector elements in the detector representing profiles along x (horizontal) and y (vertical) axes in a plane parallel to the stage in FIG. 1A. That is, the profile is a plot of measured intensity values along a selected row and column of detector elements, and represents the distribution of light intensity values that are focused from the subject surface onto the detector array. Exemplary light-intensity values measured from a subject are shown in solid lines in FIG. 3B. FIG. 3A shows the emission contours, and FIG. 3B shows the vertical profile, as determined at detector pixels corresponding to those positions.

Turning back now to FIG. 2, the spatial profile or profiles so obtained are matched or fitted with profiles stored in a database 58 of parameter-based photonic functions which are either empirical functions measured from light-emitting sources of known size and depth, or are calculated from photon-diffusion models using depth and size parameters, and optionally, other parameters, as will be described below.

From the optimal curve match, the program can make an initial estimated determination of depth and/or size and/or brightness, preferably all three, of the light-emitting source. According to a feature of the invention, the method is now carried out in a way that the depth and size determinations are refined by additional data that may be in the form of additional light-intensity data, and/or additional modeling data. For example, and as indicated in FIG. 2, the data may be in the form of:

(a) 2nd-view data, as at 62, meaning light-intensity data, typically spatial profile data, obtained by viewing the subject from a second view angle. Typically, the subject in the apparatus is tilted with respect to the optical system so that light-emission is obtained from a second region of the subject surface;

(b) Spectral data, as at 64, meaning light-intensity data obtained at one or more bandpass ranges, e.g., in a blue-light, green-light, or red-light spectral range;

(c) Transmittance data, as at 66, meaning predetermined-light intensity values obtained typically as a function of wavelength at selected locations in a subject that approximates the subject of interest;

(d) Tissue properties data, as at 68, meaning predetermined values of tissue parameters, such as reduced scattering coefficient $\mu'_s$, absorption coefficient $\mu_a$, or effective coefficient $\mu_{eff}$ corresponding to the subject tissue through which light is diffusing. This data is used, for example, to refine the spatial profile curves generated by a diffusion model;

(e) Simulation data, as at 70, meaning predetermined light-intensity values, typically spatial profile data, obtained by placing a light-source of known intensity and size at selected locations in a model representing the subject target region and adjacent surface, or in an actual subject that approximates the subject; and (f) Total intensity data, as at 72, meaning total light intensity summed or integrated over an entire spatial profile or an entire detector array.

The program run by the computation device receives the additional information at 60, and uses the information to refine the depth and size determination of the light-emitting source, at 74, as will be considered below. Finally, the refined determination of source depth, size, and optionally, shape and number of cells in the light-emitting source, is displayed to the user, either in the form of data and/or one or more subject images showing the location and intensity of the light-emitting source.

Figure 8A:
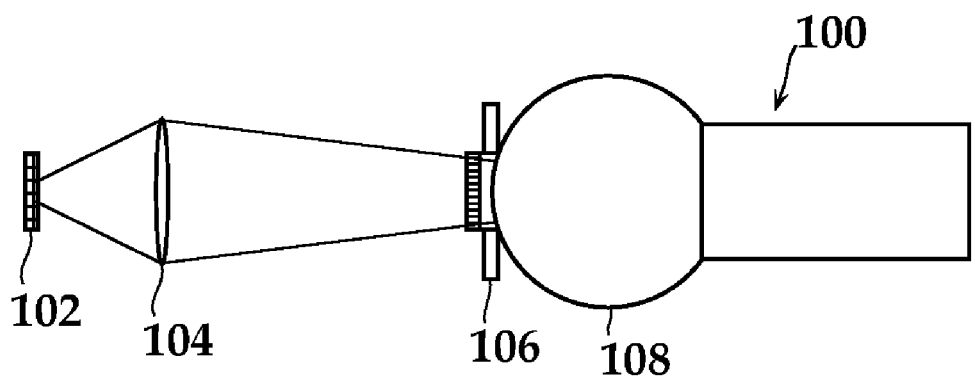
FIG. 8A illustrates components of the apparatus used for absolute calibration determination.

(g) Absolute calibrated light intensity, as at 73. Calibration to absolute intensity allows one to convert counts/sec/pixel in the CCD to radiance photons/s/cm$^2$/sr (sr=steradians). FIG. 8A illustrates an optical assembly 100 used in the calibration method. The assembly includes, in addition to a CCD detector 102, lens 104 (representing a lens assembly, as above), a bandpass filter 106 and a low-light-level integrating sphere, such as a OL Series 425 sphere available from Optronic Laboratories, which acts as a source of a known light intensity. The known radiance from the sphere, measured in photons/sec/cm$^2$/sr, allows one to calculate the calibration factor that relates the two numbers.

Figure 8B:
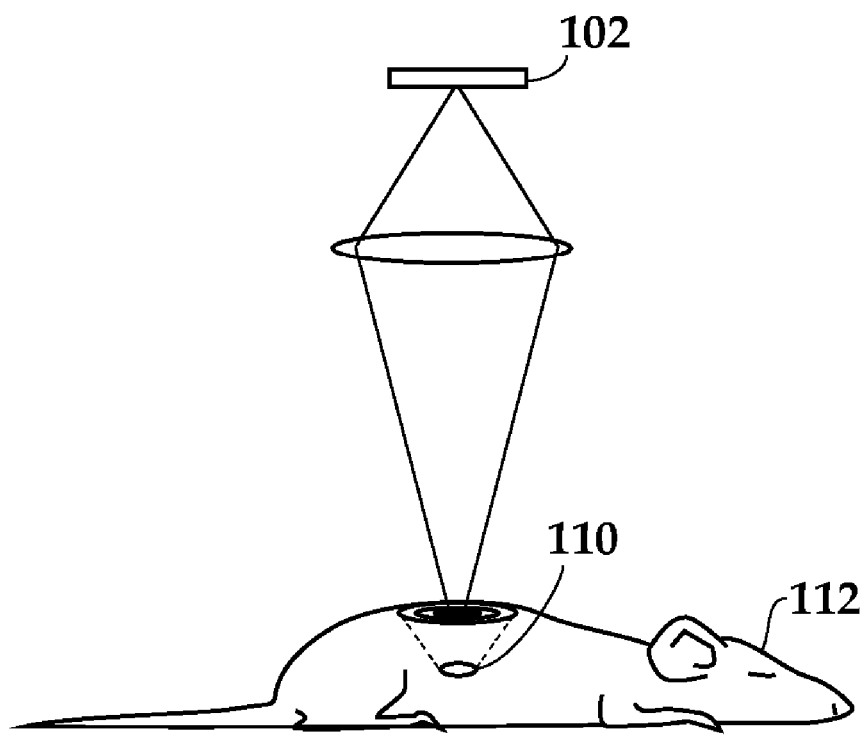
FIG. 8B illustrates how absolute calibration allows determination of cell count from an animal subject.

FIG. 8B illustrates how absolute measured intensity is used to calculate total number of cells in a light-emitting source. It is assumed that each cell will produce a photon flux $\phi_c$ photons/sec/cell. The radiance from a light-emitting source 110 in a subject 112, as measured by detector 102, measures the number of photons/s/cm$^2$/sr. The measured radiance is then integrated over a region of interest to convert to a source flux $\phi_s$ photons/sec. From the known flux values, the number of cells in the light-emitting source is readily calculated as $\phi_s/\phi_c$.

III. Light-Emission Data and Parameters

This section considers various types of light-emission data that may be collected in practicing the invention, and discusses how the data may be used in photon-diffusion modeling, and/or for determining depth or size of a light-emitting source based on curve matching with a model diffusion curve.

Light-intensity spatial profile. The basic light-emission data that is determined is a light-intensity spatial profile which has been described above, with reference to FIG. 3B. A measured light-intensity spatial profile shows the spatial distribution of light intensity emitted from the surface region of subject. The light-intensity spatial profile may be obtained along a single line, along 2 or more lines (e.g., along the x and y directions with respect to the stage supporting the subject). The entire 2D surface distribution of light may also be used. A modeled spatial profile represents the predicted light-intensity spatial distribution calculated from a model of photon diffusion through a turbid tissue. By matching a measured profile with a modeled profile, an approximate depth and/or size of light-emitting source can be determined.

Total light intensity. Total light intensity is the total light intensity summed or integrated over all of the detector elements in the detector. Total light intensity can be used as a further constraint on the fitting model used to determine source, location, and brightness.

Absolute calibrated light intensity. As described above with reference to FIG. 8B, the absolute light-intensity flux can be used to measure total flux from the light-emitting source. Assuming that this source is made up of cells which each emit an average cell flux $\phi_c$, the total number of light-emitting cells making up the source can be determined. This determination, in turn, can be used to refine the total source mass or volume determination, based on a known or estimated cell mass ratio for the tissue source.

Spectral data. Spectral data is light-intensity data collected at particular wavelength ranges, e.g., the blue-light, green-light, and red-light wavelength ranges noted above. Because light is absorbed preferentially at shorter wavelengths by subject tissue, and particularly by hemoglobin in subject tissue, the relative intensities of light at different wavelengths, can provide information about source depth and can be used in producing refined wavelength-dependent spatial profiles, based on wavelength-dependent tissue scattering and absorption coefficients.

Figure 4A:
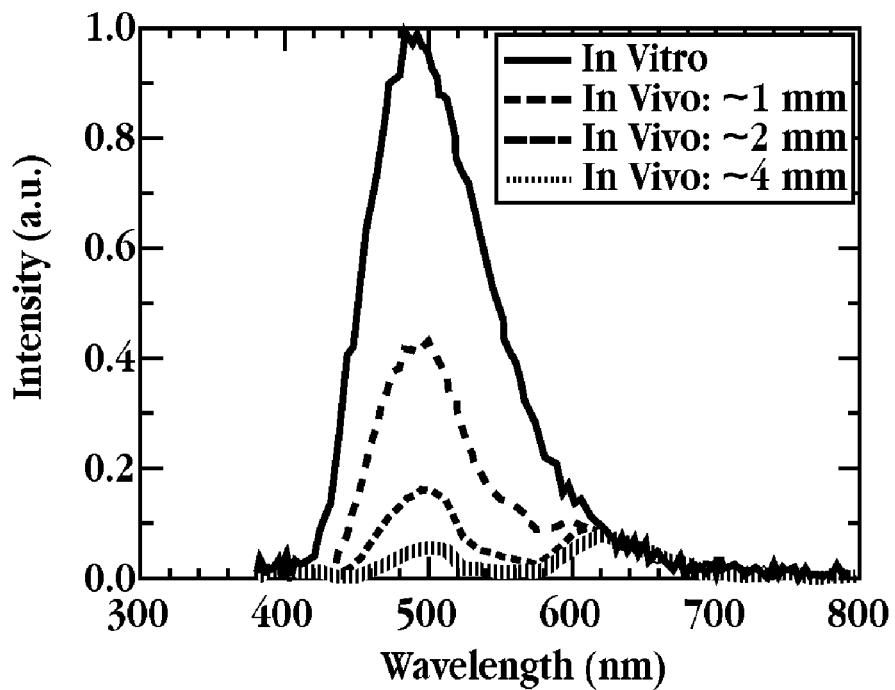
FIGS. 4A and 4B are plots of the emission spectra of bacterial luciferase in vitro (solid line), and in vivo (dashed lines) at various depths in a mouse thigh, as indicated, where the plot in FIG. 4B has been scaled to show the peak intensity in vivo in the region between 600-700 nm.
Figure 4B:
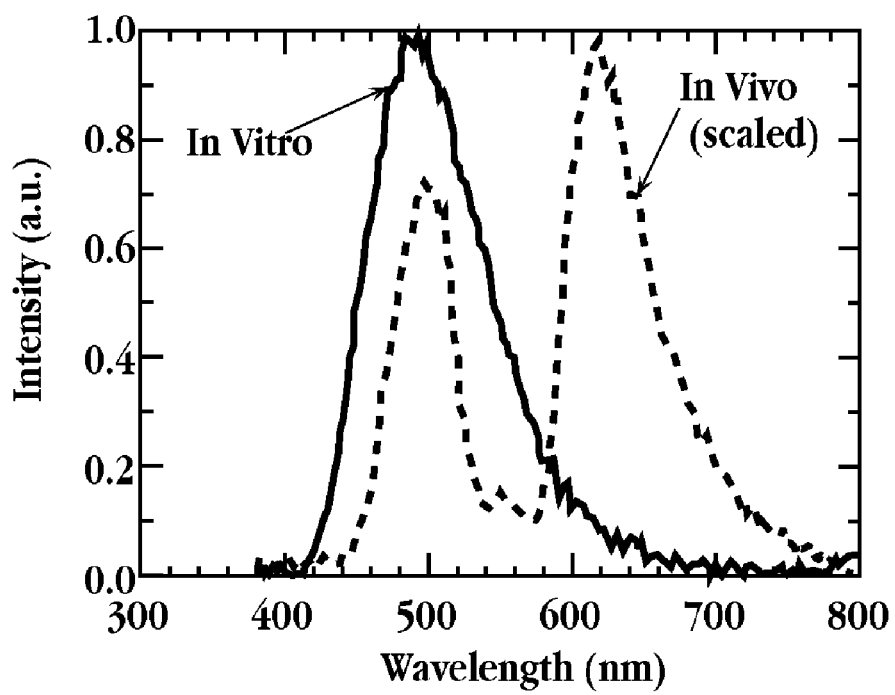

FIGS. 4A and 4B depict the differential effect distance or depth has upon light that travels through the tissue of the body region, at different wavelengths or ranges of wavelengths. The graph shows increasing light intensity on the y-axis and increasing light wavelength on the x-axis. The solid line in FIG. 4A represents the in vitro emission spectra for the light-emitting source that correlates to a zero-depth emission spectrum which comprises a broad single peak centered about 495 nm. The broad dashed line represents the emission spectrum of the light-emitting source after it has passed through about one millimeter of tissue (in vivo). At about 600 nm, the one millimeter depth emission spectrum develops a small peak, as the once large peak at about 495 nm begins to diminish in relative intensity. The intermediate dashed line represents the emission spectrum of the light-emitting source after it has passed through about two millimeters of tissue (in vivo). The 495 nm peak becomes lesser in intensity, while the 600 nm peak increases and becomes more pronounced. Lastly, the dotted line represents the emission spectrum of the light-emitting source after it has passed through about four millimeters of tissue (in vivo) where the 495 nm peak has been further reduced.

FIG. 4B represents the emission spectrum at four millimeters depth of tissue scaled against the zero tissue depth emission spectra. The 600 nm peak is prominent over the once prominent 495 nm peak. In this example, it is the ratio of the 600 nm peak to the 495 nm peak that provides information about the depth of the light-emitting source.

Preferred methods of the invention employ self-scaling computations so that the depth of the light-emitting source may be determined independent of its overall intensity. To achieve this end, functions are formulated that utilize ratios of two or more ranges of wavelengths, where each range of wavelengths travels through tissue in a body region at different rates as a function of depth of the target from the surface of the body region.

Through-body transmittance. Through-body transmittance is measured by placing a know-intensity light-source at a selected location against or inside a subject, and measuring the light-intensity that is transmitted through the subject on multiple surfaces. The transmittance will have a strong spectral component, owing to the strong spectral dependence of the scattering and absorption coefficients of different tissues (see below). Typically, transmittance values are pre-determined using a model subject, by measuring total transmittance at various selected locations and at each of a number of spectral ranges.

Figure 5:
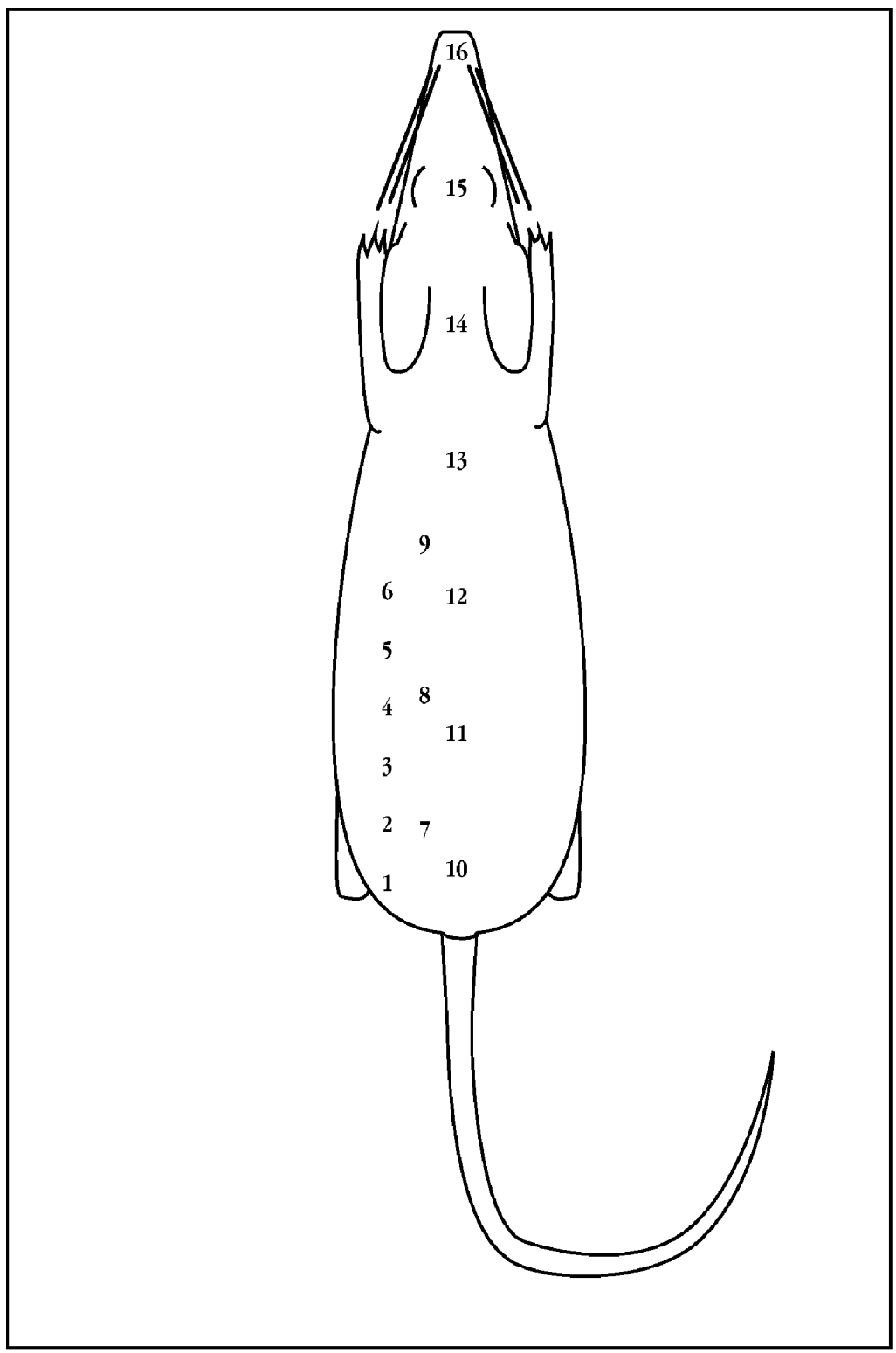
FIG. 5 shows various locations in an animal at which transmission spectra were obtained.

FIG. 5 shows a top view of a subject having a plurality of body regions indicated by numbers 1-16. In this example, the subject is an immobilized mouse, and each body region corresponds to pre-determined regions of interest. Prior to depth determinations by the practice of the methods of the invention, the subject is optically analyzed to develop a data file of optical characteristics for each body region. In this example, each body region is placed between a spectral light source and a spectral detector. Light transmission spectra are obtained for each body region. The result is analogous to placing each body region in a spectrophotometer cuvette and measuring the spectral profile of each region at different wavelengths and wavelength ranges, to create a data file of how light transmits through different body regions, and the tissues within such regions. The device of FIG. 1 may be used to develop similar data for particular ranges of wavelengths provided the device is adapted to trans-illuminate, with respect to the detector, the subject at each body region tested. Thus, the device of FIG. 1 becomes, in essence, a whole animal spectrophotometer.

Figure 6A:
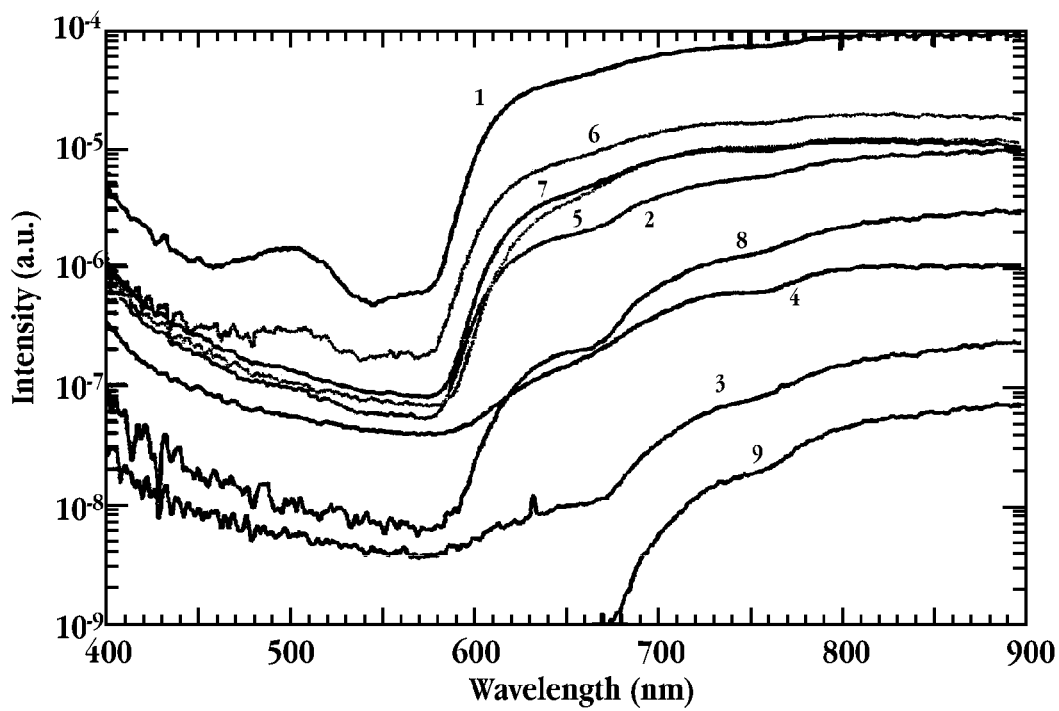
FIGS. 6A and 6B show transmission spectra through a live experimental animal at the various animal locations shown in FIG. 5.
Figure 6B:
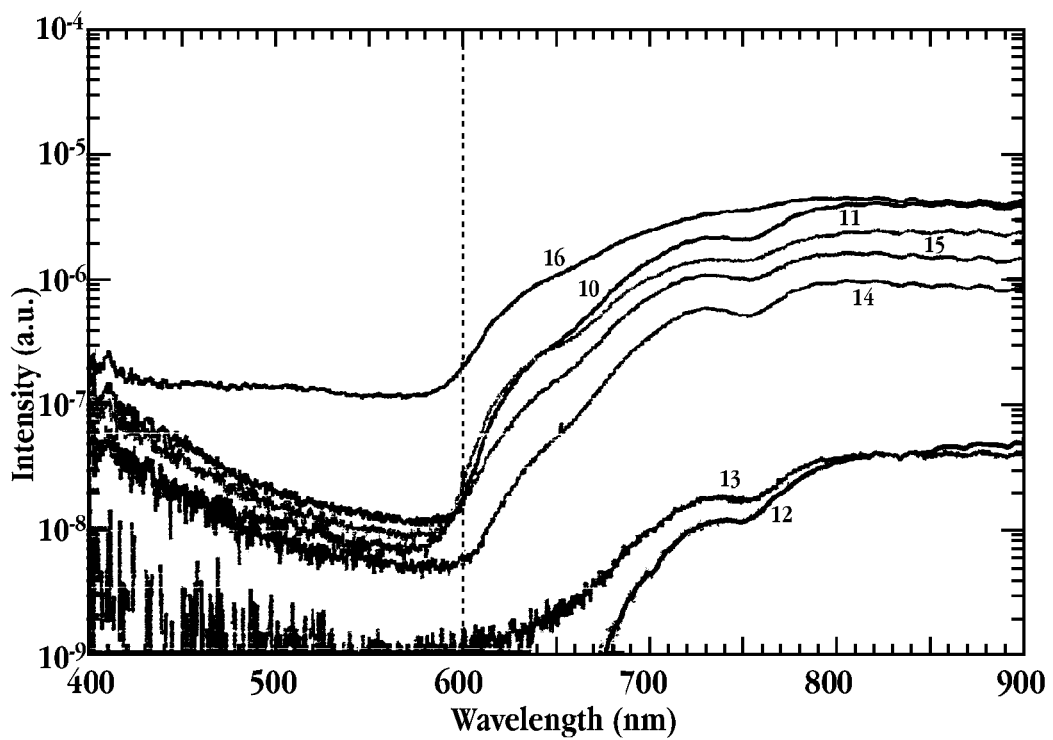

FIGS. 6A and 6B show the empirical spectral data gathered from the spectral analysis described immediately above. As is described below in more detail, this data, either as whole spectra, or particular ranges within each spectrum, can be used to create the data files for comparison with detected intensity information, or for developing functions to compute target depth.

In a more detailed approach, the apparatus provides a whole body scanner for scanning an entire subject, or portions thereof, which further comprises a scanning two-color laser for scanning the body of a subject. The scanner moves through an arc laser light of at least two colors, either simultaneously, or sequentially. As the laser light beams upward, it penetrates the body of a subject placed within a rotational tube. The detector placed opposite the laser light source is adapted to receive and measure the laser light as it moves through its arc path.

Figure 7A:
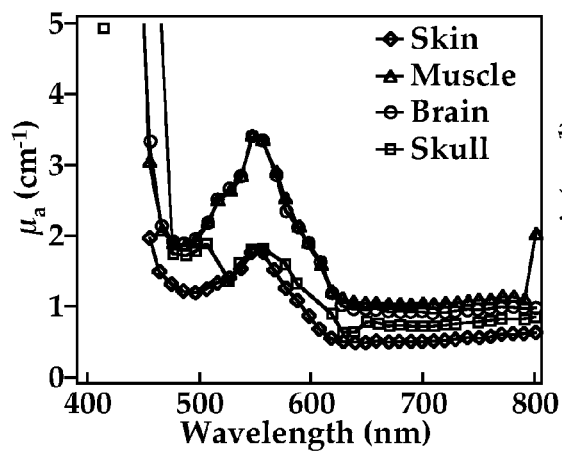
FIGS. 7A and 7B are plots of the absorption coefficients.
Figure 7C:
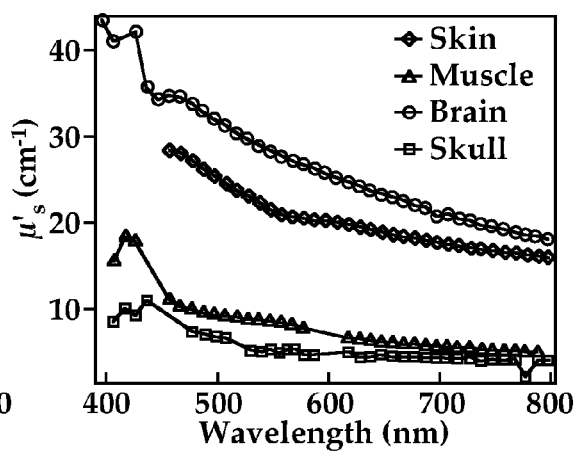
FIGS. 7C and 7D are plots of the isotropic or reduced scattering coefficients of various tissues as a function of wavelength.
Figure 7B:
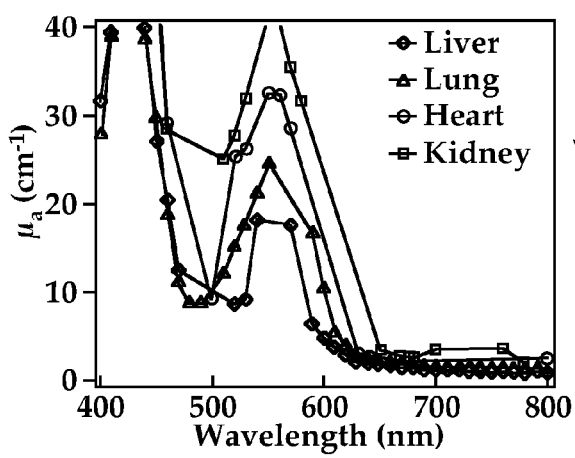

Tissue optical properties. There are two important optical properties of subject tissue used in photon diffusion modeling. The first is the absorption coefficient $\mu_a$ of the tissue, which is related to the fraction of incident light that is absorbed per unit pathlength. As seen in FIGS. 7A and 7B, which plot absorption coefficients for a variety of tissue types over the visible spectrum, the absorption coefficient is highly dependent on the nature of the tissue, and the wavelength of light, with each tissue showing a peak absorption in the 500-600 nm range. The relatively low absorption coefficient above about 600 nm is consistent with the spectral data seen in FIG. 13A, and with the total transmittance data shown in FIGS. 6A and 6B.

Figure 7D:
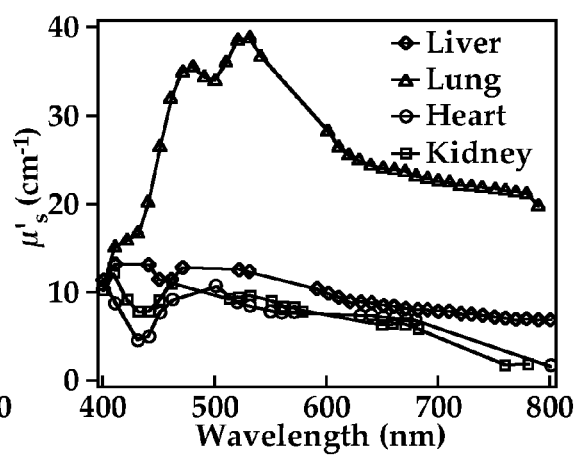

The second important optical property is the reduced scattering coefficient $\mu'_s$ of the tissue, which is the fractional decrease in intensity per unit length of penetration of light due to large angle light scattering. As seen in FIGS. 7C and 7D, which plot reduced scattering coefficient for the same tissues over the visible spectrum, scattering effects can be relatively different in different tissues. In general, the reduced scattering coefficient decreases somewhat at longer wavelengths.

Figure 6C:
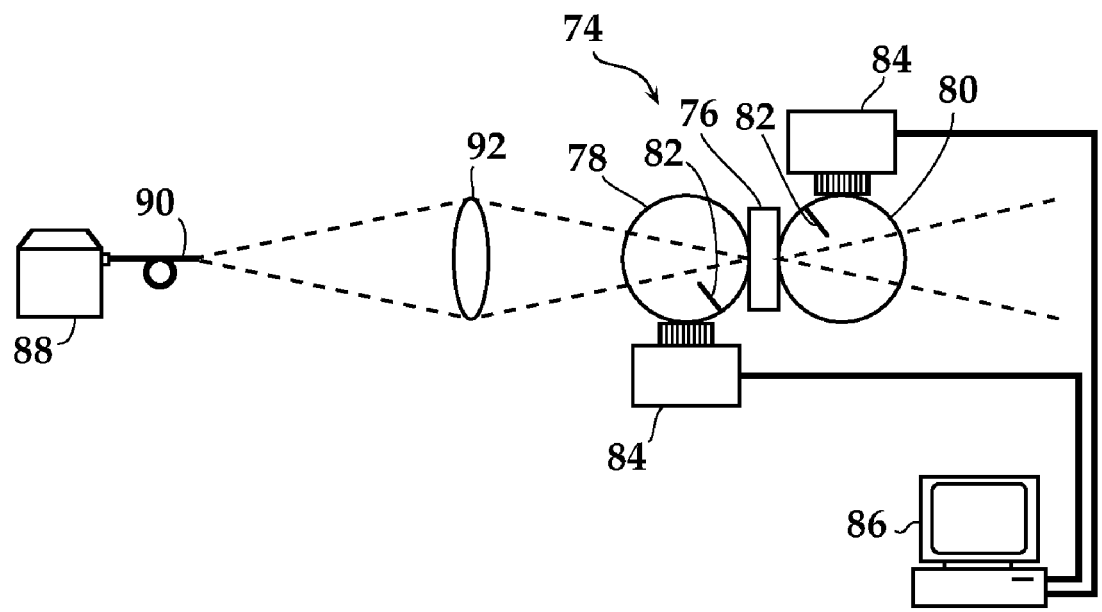
FIG. 6C illustrates a double integrating sphere apparatus useful for measuring optical properties of a sample, e.g., tissue.

A double integrating sphere (DIS) system is a widely used tool to measure the optical properties of tissue or any turbid medium since it conveniently measures the diffuse reflectance, $R_d$, and the diffuse transmittance, $T_d$, simultaneously. FIG. 6C illustrates the double integrating sphere apparatus 74 used to measure these values in order to obtain optical properties such as the absorption coefficient, $\mu_a$, and the reduced scattering coefficient, $\mu'_s$ (Prahl, S. A., et al., *Applied Optics* 32:559-568 (1993); Pickering, J. W., et al., *Applied Optics* 32:399-410 (1993)). The sample 76 is placed between the two integrating spheres 78 and 80, with internal baffles 82 positioned to prevent measurement of directly reflected or transmitted light. The spheres are coated with a highly reflective material to minimize absorption of light. Light is detected with detectors 84 and preferably analyzed using a computer 86. Sample illumination between 400-1000 nm is achieved using an arc lamp connected to a monochromator 88, via a fiber optic cable 90 and lens 92.

From diffuse reflectance, $R_d$, and diffuse transmittance, $T_d$, values, the absorption and the reduced scattering coefficients are obtained using the inverse adding-doubling program (http://omic.ogi.edu/software/iad/index.html). This program is a numerical solution to the one speed radiative transport equation, which describes light propagation at steady state in a scattering medium (Prahl, S. A., et al., *Applied Optics* 32:559-568 (1993)). The program is an iterative process, which estimates the reflectance and transmittance from a set of optical parameters until the calculated reflectance and transmittance match the measured values.

A characteristic of the DIS system is the fact that tissues need to be extracted before the measurement. Therefore, it is desirable to maintain tissue viability under measurement conditions. Vascular drainage of hemoglobin and tissue hydration need to be considered, especially at wavelengths where hemoglobin and water absorption are high. Partly in view of the foregoing, a preferred method of measuring tissue optical properties is a non-invasive in vivo measurement, as follows.

Figure 6D:
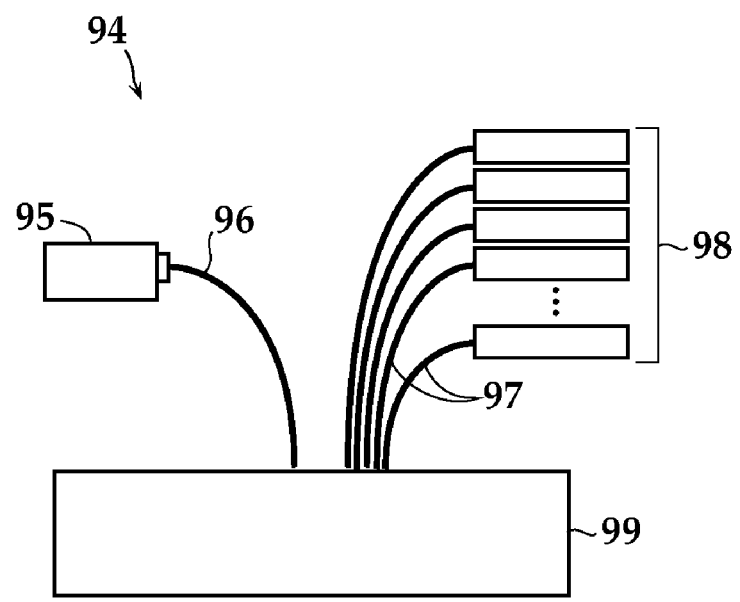
FIG. 6D illustrates the experimental set up of a radial fiber probe, useful for measuring optical properties of tissue in vivo.

A radial fiber probe similar to that described by Bevilacqua (Bevialcqua, F., et al., *Applied Optics* 38:4939-4950 (1999)) may be used to measure optical properties non-invasively or with minimal invasiveness in vivo. FIG. 6D illustrates an experimental set up of a radial fiber probe 94. Fiber probe 94 includes an illumination source 95, at least one illumination fiber 96 and several (e.g., six) detection fibers 97 generally within a 1-2 mm distance. The probe is then place perpendicularly on a tissue of interest 99, preferably with minimal contact pressure. The output of the detection fibers 97 is fed into a set of corresponding detectors 98. The optical properties are spatially resolved from intensity versus radial distance from the source. At small source-to-detector separations, simple analytical models such as the diffusion approximations are not well suited to describe the system therefore Monte Carlo methods are typically used to analyze the data.

IV. Photon Transport Models

This section considers photon-transport models for simulating photon emission at the surface of a body from a light source below the surface and moving through a turbid medium. In particular, it is desired to generate simulated light-intensity spatial profiles based on (i) depth of the light-emitting source, (ii) size of the light-emitting source, and (iii) light-absorption and light-scattering coefficients. Since the light-absorption and light-scattering coefficients are dependent both on wavelength and on the nature of the tissue through which the photons diffuse, the model may be refined to specifically consider the nature of the tissue and the spatial profiles at selected wavelengths.

The photon-diffusion model employed herein makes a number of simplifying assumptions for purposes of generating an initial light-intensity spatial profile from which initial source-depth and source-size information can be generated, as will be considered in Section V. The model may then be expanded by considering additional tissue-dependent and/or wavelength dependent information to refine the spatial profile, for purposes of improving the curve fit with a measured spatial profile. Alternatively, the initial depth and size information can be refined by other types of curve or data matching. Both approaches for refining the initial depth/size approximation will be considered in Section V below.

Figure 9A:
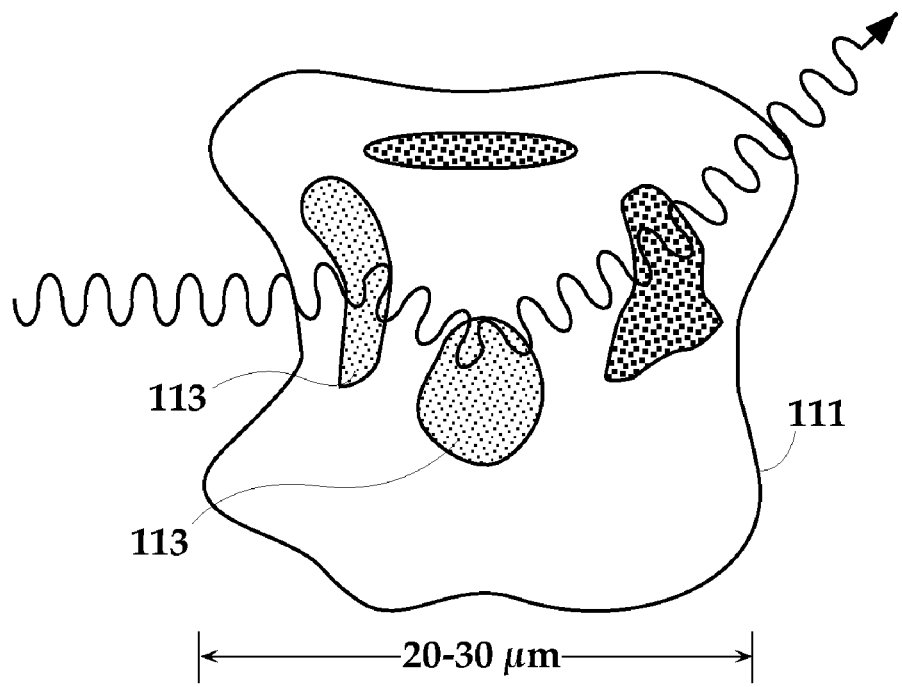
FIGS. 9A and 9B illustrate how photons diffuse through tissue (9A) and how the photons that diffuse to the surface of the tissue are captured in the invention (9B).

FIG. 9A shows a photon path as it diffuses through a turbid tissue formed of cells, such as cell 111 containing organelles 113. As seen, the cell size, typically in the 20-30 micron size range, is large relative to the wavelength $\lambda$ of light, which is between about 0.4 and 0.6 microns. Scattering is due to abrupt discontinuities ($\ll\lambda$) at membranes and is characterized by an inverse length scattering coefficient $\mu_s$ of about 10-20 $mm^{-1}$. The scattering anisotropy g is about 0.9, which gives a reduced scattering coefficient $\mu'_s=\mu_s(1-g)$, or about 2 $mm^{-1}$. The absorption coefficient $\mu_a(\lambda)$ is between 0.01 and 1 $mm^{-1}$, and as seen above, has a strong wavelength dependence. The absorption and scattering coefficients are wavelength-dependent, but for $\lambda > \sim 600$ nm, it is generally true that $\mu_a \ll \mu'_s$ in tissue.

A quantitative description of transport of light from a target site within a body to a light detector located adjacent a body surface may be achieved by a solution of a radiative transfer diffusion equation of light with appropriate boundary conditions (e.g., R. C. Haskel; et al in "Boundary conditions for the diffusion equation in radiative transfer", J. Optical Soc Am., 11A:2727 (1994)). One approach, for example, uses an extrapolated boundary condition shown schematically in FIG. 9B in which optical fluence vanishes at a planar surface that is displaced from the physical boundary at a distance $z_b$ that takes account of the Fresnel reflection of light at the physical boundary.

Figure 9B:
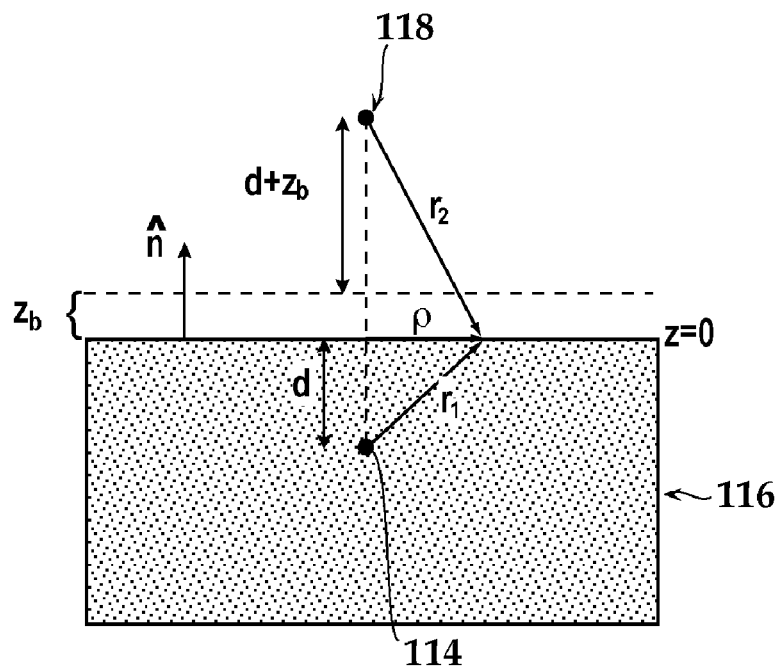

As a first approximation, the body in which the light-emitting source is located is represented as a semi-infinite, homogenous turbid medium that is both scattering and absorbing. The approximation is illustrated in FIG. 9B which shows a light-emitting point source 114 in slab 116 a distance d below the slab surface. The diffusion equation is $$D\nabla^2\phi(r) = \mu_a\phi(r) - S(r) \tag{1}$$

and Fick's law is $$j(r) = -D\nabla\phi(r) \tag{2}$$

where $\phi$ is the isotropic fluence (watts/m$^2$), j is the small direction flux (watts/m$^2$), S is the power density (watts/m$^3$), r is the radius, and $$D = \frac{1}{3[(1-g)\mu_s + \mu_a]} \tag{3}$$

The Green's function solution for a point source P (watts) is $$\phi(r) = \frac{P}{4\pi D r}\exp(-\mu_{eff} r) \tag{4}$$

where $\mu_{eff} = \sqrt{3\mu_a(\mu'_s+\mu_a)}$ and $\mu'_s=(1-g)\mu_s$.

The solution to the diffusion equation in slab geometry using the extrapolated boundary condition is obtained by summing contributions from the source 114 plus image source 118 (as shown in FIG. 9B), resulting in the following equation for radiance at the surface (viewing perpendicular to the surface) for a point source P (watts) at a depth d.

$$L_{z=0} = \frac{1}{4\pi}\left(\frac{P}{4\pi D}\right)\left\{\begin{array}{c}\frac{\exp(-\mu_{\mathit{eff}}r_1)}{r_1} - \frac{\exp(-\mu_{\mathit{eff}}r_2)}{r_2} + \\ 3D\left[\begin{array}{c}\frac{d}{r_1^2}\left(\mu_{\mathit{eff}} + \frac{1}{r_1}\right)\exp(-\mu_{\mathit{eff}}r_1) + \\ \frac{d+2z_b}{r_2^2} \times \left(\mu_{\mathit{eff}} + \frac{1}{r_2}\right) \\ \exp(-\mu_{\mathit{eff}}r_2)\end{array}\right]\end{array}\right\} \quad (5)$$

where $r_1 = \sqrt{\rho^2 + d^2}$, $r_2 = \sqrt{\rho^2 + (d+2z_b)^2}$ $\rho$ is the radius on the slab surface and $$z_b = \frac{1 + R_{\mathit{eff}}}{1 - R_{\mathit{eff}}} \frac{2}{3(\mu_a + \mu_s')} \quad (6)$$

and $R_{\mathit{eff}}$ is the effective reflection coefficient which is about 0.43 for tissue.

Plotting surface radiance as a function of $\rho$ gives the plot shown in the solid line in FIG. 10B, which has the same derivation as the light-intensity profile plot shown in dotted lines in FIG. 3B.

The spatial profile curve for a light-emitting point in a turbid medium was also calculated using a much more computationally intensive Monte Carlo simulation, which follows each photon through a random walk, as illustrated in FIG. 10A. The Monte Carlo simulation, shown in "+" symbols in FIG. 10B closely matches the spatial profile calculated from the diffusion equation.

To illustrate how the diffusion equation may be used to model photon diffusion through various tissues and a various depths, the spatial profile was calculated for various values of $\mu_{\mathit{eff}}$, corresponding to $\mu_a$ and $\mu_s'$ values of 2.0 and 20 cm$^{-1}$, respectively, for $\mu_{\mathit{eff}}=11$ cm$^{-1}$; 0.4 and 10 cm$^{-1}$, respectively, for $\mu_{\mathit{eff}}=3.5$ cm$^{-1}$, and 0.05 and 5 cm$^{-1}$, respectively, for $\mu_{\mathit{eff}}=0.87$ cm$^{-1}$. The three values of for $\mu_a$ correspond roughly to tissue absorption for blue, green, and red wavelengths.

The plots in FIGS. 11A and 11B show that intensity decreases and spot width increases with increasing depth, and that large values of $\mu_{\mathit{eff}}$ result in large attenuation of peak intensity with narrower spot width.

V. Determining Depth and Size Information

In practicing the method of the invention, the subject is initially treated to localize light-emitting molecules at a target source, as detailed above. The subject is then placed at a selected location within the light-tight chamber of apparatus 20 (appropriately scaled for subject size) and the optical system is adjusted to measure light emission events from the source at the surface region of the subject between the light-emitting source and the detection optics. With the subject immobilized at a selected optical perspective, a light-intensity spatial profile of surface light emission is obtained, also as described above. FIG. 3A is a surface map of measured light intensity from a subsurface light source, which was subsequently used to generate the spatial profile shown in FIG. 3B.

Figure 12A:
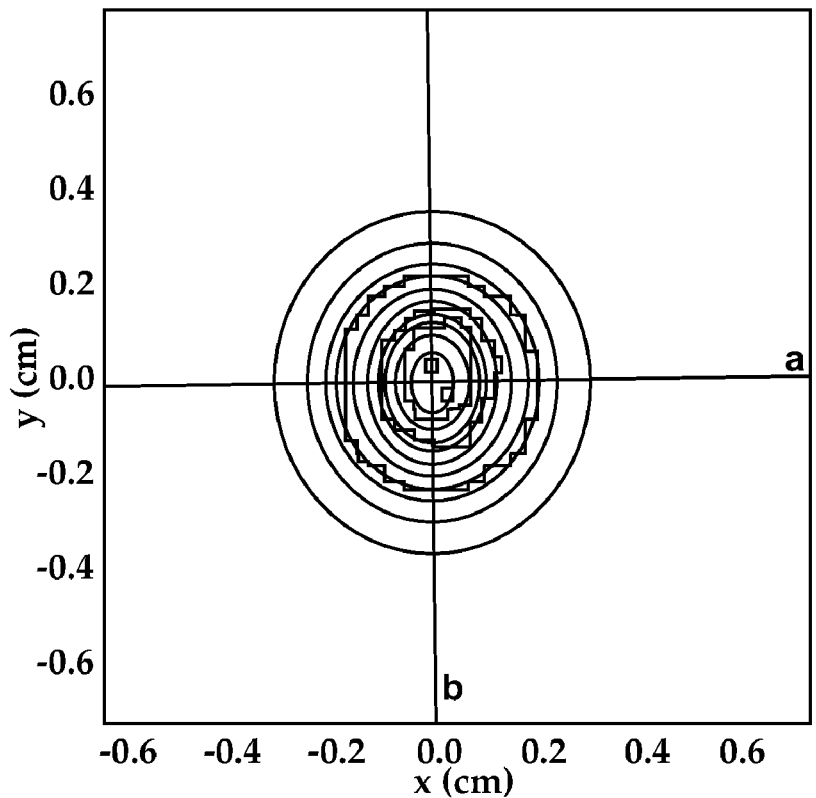
FIG. 12A is a surface light-intensity image from a light-emission source in a subject, and shows the horizontal and vertical profile lines along which light-intensity profiles were measured.

The spatial profile(s) are then fitted with parameter-based biophotonic functions that relate light-emission intensity to depth of a light-emitting source (and in some cases, source size) to obtain an initial determination of source depth (and in some case, source size). One preferred biophotonic function is that derived from the simplified diffusion model discussed in Section IV above, in which light intensity from a point source or source having a defined spherical or ellipsoidal volume is calculated as a function of source depth, fixed scattering and absorption coefficients, and surface distance r from the source. Conventional non-linear least-squares curve fitting techniques, such as Levenberg-Marquardt ("Numerical Recipes in C", Press et al., eds, Cambridge Press, NY, 1989) are suitable for the curve fitting. Curve fitting can be done using a single 1-dimensional ("1-D") profile, as shown in FIG. 3, a plurality of such profiles, or the entire 2-D spatial distribution (e.g., as shown in FIG. 12A). Curve-fitting calculations to the data shown in FIG. 3B (dashed line) indicate a depth of 2.7 mm, which compares well with the estimated actual depth of 2.2 mm.

Figures 12B, 12C:
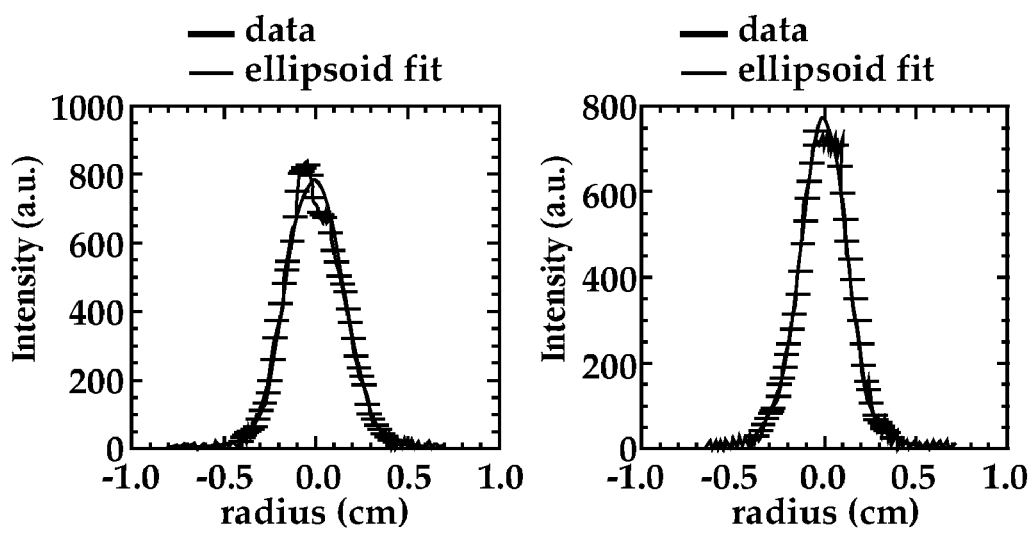
FIGS. 12B and 12C are light-intensity profiles measured along the horizontal and vertical profile lines shown in FIG. 12A.

FIGS. 12A-12C give another example of how depth and size information can be determined from spatial profiles. The light-emitting source here is a subcutaneous elliptical tumor having actual dimensions in the horizontal and vertical directions of 2.7 mm and 3.2 mm, respectively, and a tumor thickness of 1.5 mm. The horizontal and vertical profiles were (FIGS. 12B and 12C, respectively) were fitted with curves generated for an ellipsoid light-emitting source having horizontal and vertical dimensions of 1.3 and 2.4 respectively, a thickness of 1.5 mm, and a depth of 0.4 mm.

The source depth (and optionally, source size) determination from the initial curve fitting can be refined, and source size approximated, by employing additional data whose effect is to refine the parameters of the biophotonic function. The nature of the additional data, and the manner in which it refines the parameters, e.g., depth and size, of the biophotonic function, providing refined depth and source-size information, will now be considered for each of the information types outlined in Section II above, with respect to FIG. 2.

A. 2nd-View Information.

To obtain 2nd-view data, the subject is rotated with respect to the viewing and detection optics for viewing the light-emitting source from another perspective. From this second perspective, a second light intensity profile is obtained, providing a second depth determination with respect to a second subject surface region. By determining the intersection of the source depths at two different surface locations, a more accurate depth and/or source size can be determined. The more views that are obtained, the more accurately depth and source size can be determined.

B. Spectral Data.

A target's depth within a body region may be determined, or the target depth refined, by (i) causing the target to emit light at two or more wavelength ranges, and (ii) comparing the differences in each range's light transmission through the body region, at a surface of the body region, provided that the light in each wavelength range transmits through the body region differently from the light in other wavelength ranges as a function of depth.

Typical spectral curves (representing total light intensity at the indicated wavelengths) as a function of source depth are shown in FIG. 4A, discussed above. As seen particularly in FIG. 4B (where the peaks are scaled to the in vitro spectral curve), the ratio of peak height at above 600 nm, e.g., 620 nm, to that the in vitro (zero-depth) peak height, e.g., around 500 nm, increases dramatically as a function of depth. Thus, by generating a spectral curve and determining the ratio of peak heights, typically above and below 600 nm, e.g., 620 nm: 500 nm, accurate depth information based on the wavelength-dependent loss in intensity in turbid tissue, can be determined.

A useful formula for determining approximate depth from spectral measurements can be derived from Eq. 4 as follows:

$$d \approx \frac{\ln(\phi_1 D_1 / \phi_2 D_2)}{\mu_{eff2} - \mu_{eff1}} \quad (7)$$

where d represents depth, $\phi$ represents the measured light intensity, $\mu_{eff}$ represents the empirically determined effective coefficient of attenuation, and D is the empirically determined diffusion coefficient. The subscripts 1 and 2 in the above formula refer to two separate wavelengths at which measurements are made.

Using the above formula, depth may be determined from two or more light intensity measurements at different wavelengths or ranges of wavelengths. In one embodiment, the depth may be obtained by executing the following series of steps: (1) Image the bioluminescent cells in vitro as well as in vivo (in the animal) at two wavelengths; (2) Quantify the images by measuring, e.g., the peak intensity or the average (integrated) intensity for each image; (3) Calculate the ratio of the in vivo image data to the in vitro image data at each wavelength; and (4) Calculate the depth using Equation 7 and an effective scattering coefficient $\mu_{eff}$ obtained, e.g., from tissue property measurements. An application of this approach is illustrated in Example 1.

In one embodiment, it is preferable to have a significantly different value for each $\mu_{eff}$. Animal tissue provides such a difference in $\mu_{eff}$, due largely to the presence of hemoglobin, which has a large absorption peak just below 600 nm, and relatively low absorption above 600 nm.

Alternatively, the additional spectral data may include one or more spatial profiles taken at one or more selected wavelengths or wavelength ranges. The profile(s) are then compared with model intensity functions generated, for example, from a photon diffusion model above, using wavelength-specific values for the absorption, scattering, and/or effective coefficients, as described above with respect to FIG. 3B.

Figure 13A:
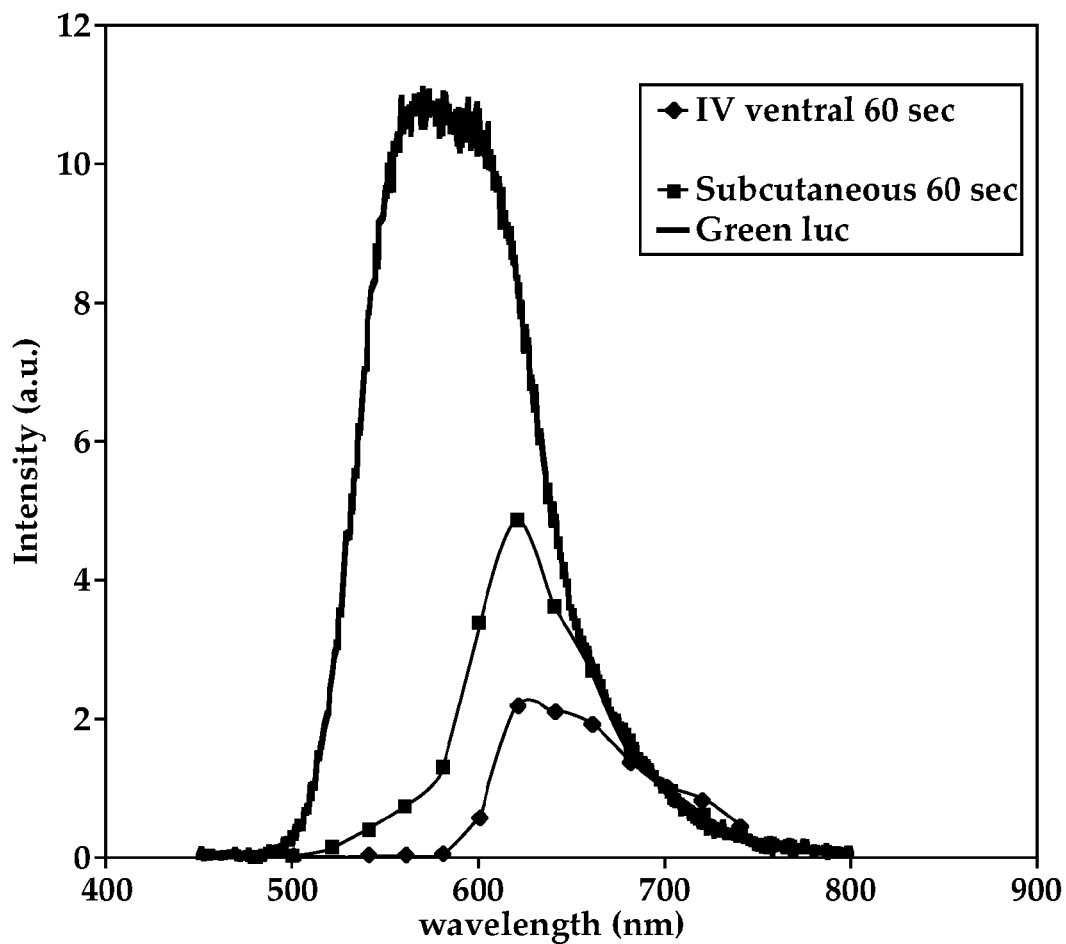
FIG. 13A shows spectral image plots of luciferase light-emitting sources acquired in vitro (solid line), from the subcutaneous site shown in FIG. 13B (squares); and from the lung sites seen In FIG. 13C (diamonds).
Figure 13B:
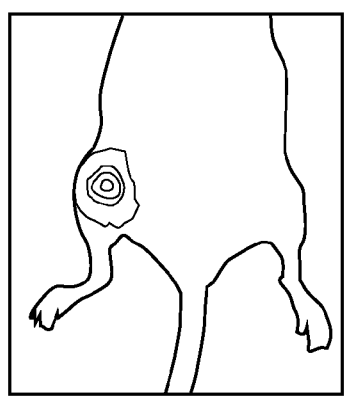
FIGS. 13B and 13C are surface light-intensity images from animals with a subcutaneous light-emitting source (FIG. 13B) and light-emitting sources in the lungs (FIG. 13C).
Figure 13C:
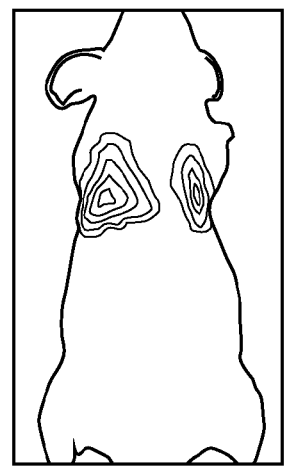

In still another application, intensity values can be measured at discrete wavelengths, spaced every 20 nm. The spectral plots in FIG. 13A show green luciferase in cells in PBS solution, and spectral curves for green luciferase localized subcutaneously at a site indicated in FIG. 13B and in the lungs as shown in FIG. 13C. All the curves are normalized to a value of 1 at 700 nm. The ratio of intensities at 560 nm to 620 nm is indicative of depth.

As noted above, a related aspect of the invention provides a method of determining the depth of a light-emitting source in a subject. In practicing the method, the light emission intensity from the subject at two or more different wavelengths between about 400 and about 1000 nm. The depth of the light-emitting source is determined using the measured light-emission intensities, and information related to the optical properties of the subject, e.g., coefficients of attenuation and diffusion in the subject.

Information relating to the optical properties, e.g., coefficients of attenuation and diffusion in the subject may be obtained by direct measurement of the coefficients in material that is the same or similar to that of the subject. This information, combined with measured intensities at two wavelengths in vitro (zero depth) and in vivo (the depth to be determined) can be applied to Equation 7 to determine the depth of the light source, as described above, and as illustrated in Example 1.

Alternatively, optical-properties information may be obtained indirectly, by determining, at two or more different wavelengths, light intensities from a light-emitting source located at each of a two or more of a plurality of depths in tissue or material corresponding to that of the subject. The desired depth determination is then made by matching the measured light intensities, e.g., the ratio of the intensities at the different wavelengths, with the light intensities determined at each of the plurality of depths. In a more specific approach, the spectral profile of light intensities from the light-emitting source may be compared (matched) with each of a plurality of spectral profiles of light intensities from a light-emitting source at each of a plurality of depths.

C. Through-Body Transmittance Data.

Through-body transmittance data is obtained as described above, and illustrated in FIGS. 5, 6A and 6B for a small-animal subject. As noted above, the information provides a wavelength dependent light-transmission value through a selected tissue or tissues of a known thickness. Predetermined transmittance data from a number of selected locations in a subject can be used to estimate average whole-body scattering and absorption coefficients at the different subject locations, for purposes of refining the modeled spatial profile, either over the entire visible spectrum, or at selected wavelengths, used for curve fitting to the measured spatial profile.

D. Tissue Properties Data.

The tissues property data, such as that shown in FIGS. 7A-7D, typically includes wavelength dependent absorption and scattering coefficients for each of the major body tissues. This data is used, for example, in the above model of photon diffusion, to refine the spatial profiles that would be produced by light transmission through a given tissue, at a given wavelength, typically in the red wavelength. Thus, for example, if the light-emitting source in the subject is muscle, and the spatial profile is taken in the red wavelength, a refined spatial profile generated with the tissue-specific and wavelength-specific absorption coefficient will provide a refined spatial profile curve for curve fitting with the measured curve.

E. Simulation Data.

In another embodiment, a test point or otherwise known-shape light-emitting source may be introduced into a block or slab that simulates turbid tissue. The block can be prepared with various scattering and diffusion coefficients, and various shapes to simulate light-emitting source conditions in a subject. Upon placement of the test point, spectral profiles may be taken from the outer surface of the body region where the test point was placed. This data then is correlated with the actual depth and location of the test point. By moving the test point from point to point within the block, a series of spectral measurements can be made. From this series of spectral measurements, a data file can be assembled to model the spectral responses of different regions within the subject.

F. Integrated Light Intensity

Summed or integrated light-intensity, as noted above, refers to the light-intensity summed over all or some defined area of the detector array. The integrated light intensity can be compared with the integral of Equation 5 to provide yet another estimate of source depth and brightness. This information can be used in conjunction with the profile information. The integrated light intensity can also be calculated for multiple wavelengths.

G. Calibrated-Intensity Data.

In the absence of calibrated intensity data, intensity measurements may vary from camera to camera, and measured values will depend on variable such as field of view, binning, time, and f-stop.

Absolute calibrated intensity (Section III above), allows one to refine the depth-of-source determination, based on curve fitting to true peak value, and to estimate the number of bioluminescent cells in tissue, as discussed in Section III above.

In still other embodiments, the invention provides for the integration of other imaging data with the intensity and spatial distribution data to produce greater detail three-dimensional maps of the subject and target located therein. For example, compiled differential light transmission data, such as disclosed above, may be interlaced with coordinate systems derived from other three dimensional imaging systems such as stacked slices of MRI images forming a three dimensional digitized "image" or coordinate system. Such a coordinate system may then be used to better illustrate the anatomy of the subject for which a target is being identified. In the case where the subject is a laboratory animal such as a rat, such animals are highly uniform in structure from one animal to the next for a given strain. Consequently, a coordinate data, spectral data, and spatial intensity pattern files may be developed by a commercial vendor, and sold for use with simplified detection units such as shown in FIG. 1. If model three-dimensional information is supplied as a data file, then user units do not need to be equipped for three-dimensional scanning and mapping. The two-dimensional images contemplated in the methods and apparatuses disclosed above may be combined with the three-dimensional data files provided by the vendor to yield complete three dimensional information about the size, shape, depth, topology, and location of a target within the subject.

The following examples illustrate, but in no way are intended to limit the present invention.

EXAMPLE 1

Calculating Depth of a Light-Emitting Object Using Two-Wavelength Spectral Images The spectral information shown in FIG. 13A was used to calculate the depth of luciferase-labeled cells in an animal that received a sub-cutaneous injection of the cells (FIG. 13B) and an animal having labeled cells in its lungs (FIG. 13C). The analysis was performed using data at wavelengths equal to 600 nm and 640 nm using the following steps: (i) the bioluminescent cells were imaged in vitro as well as in vivo at 600 nm and 640 nm; (ii) the images were quantified by measuring the average intensity for each image; (iii) the ratio of the in vivo image data to the in vitro image data were determined at each wavelength; and (iv) the depth was calculated using Equation 7 and an average effective scattering coefficient eff estimated from the absorption and scattering coefficients in FIG. 7.

For the subcutaneous cells, the ratios of in vivo to in vitro intensities (relative intensities, or $\phi$) are 0.35 and 0.75 at 600 nm and 640 nm, respectively. For the lung signals, these same ratios are 0.05 and 0.47. Using $\mu_a=0.25$ mm$^{-1}$ and $\mu_s'=1.0$ mm$^{-1}$ at 600 nm and $\mu_a=0.05$ mm$^{-1}$ and $\mu_s'=1.0$ mm$^{-1}$ at 640 nm results in $\mu_{eff}=0.97$ mm$^{-1}$ at 600 nm and 0.4 mm$^{-1}$ at 640 nm. The values of the diffuse coefficient D are 0.27 mm and 0.32 mm at 600 nm and 640 nm respectively. Substituting these numbers into Equation 6, reproduced below, $$d \approx \frac{\ln(\phi_1 D_1 / \phi_2 D_2)}{\mu_{eff2} - \mu_{eff1}}$$

(in this case, subscript 1 refers to 600 nm and subscript 2 refers to 640 nm), results in d=1.6 mm and d=4.0 mm for the subcutaneous and lung depths, respectively.

Although the invention has been described with respect to particular embodiments and applications, it will be appreciated that various changes and modification can be made without departing from the invention.

It is claimed:

1. A method of investigating the location and light intensity of a light-emitting source in a subject, comprising:
   obtaining a first measured light intensity profile by measuring, from a first perspective relative to a photodetector device, photons that (i) originate from the light-emitting source in the subject, (ii) travel through turbid biological tissue of the subject, and (iii) are emitted from a first surface region of the subject;
   fitting the first measured light intensity profile with a parameter-based biophotonic function to obtain an initial determination of the location and light intensity of the light-emitting source; and
   refining one or more parameters of the biophotonic function to obtain an approximate depth and light intensity of the light-emitting source in the subject.

2. The method of claim 1, wherein the refining includes using data relating to the wavelength of photons emitted from the surface of the subject.

3. The method of claim 2, for use in investigating the depth of the light-emitting source in the subject, wherein said refining includes (a) measuring light emission intensity from the subject at two or more different wavelengths between about 400 and about 1000 nm, (b) obtaining information related to optical properties in the subject's tissue, and (c) using the measured light intensities and the obtained information to refine the depth of the light-emitting source.

4. The method of claim 3, wherein (b) includes measuring the coefficients of attenuation and diffusion in tissue or material corresponding to that of the subject, and (c) includes using said coefficients in a formula to estimate depth of said source.

5. The method of claim 4, wherein obtaining said data includes (i) measuring total light intensity from the first surface region of interest, (ii) estimating tissue-region depth, light intensity, and brightness by comparing the measured light-intensity values with total radiance values generated as a function of depth of a point-source light emitters, wherein the total radiance values are generated from a model of photon-diffusion from a light source of defined light intensity, shape, and/or depth below a body surface.

6. The method of claim 5, wherein said refining includes using data obtained from a second measured light intensity profile, said second profile being constructed by measuring, from a second perspective with said photodetector device, photons which (i) originate from the light-emitting source, (ii) travel through turbid biological tissue of the subject, and (iii) are emitted from a second surface region of interest of the subject.

7. The method of claim 1, wherein said refining includes using data obtained from a computer simulation of the diffusion of light from a light-emitting source in a turbid medium.

8. The method of claim 7, wherein said computer simulation is a photon diffusion model.

9. The method of claim 8, wherein said refining comprises (i) generating a plurality of theoretical light-intensity profiles, based on a model of photon diffusion from a light-emitting source located at one of a plurality of depths, and having one of a plurality of light intensities and shapes, through a turbid medium having absorption and scattering properties similar to those of biological tissue, (ii) comparing the quality of fit between each of said plurality of theoretical light-intensity profiles and said first measured light intensity profile, (iii) selecting the theoretical light intensity profile which provides a suitable fit to the first measured light intensity profile, and (iv) obtaining an approximate depth, shape and brightness of the source in the subject using parameters from the theoretical light intensity profile selected in (iii).

10. The method of claim 1, wherein said light-emitting source includes a fluorescent light source.

11. The method of claim 1, further comprising using the approximate depth and shape of the source in the subject and superimposing a three-dimensional visual representation onto an image of the subject.

12. A method of investigating the location and size of a light-emitting source in a subject, comprising:
   obtaining a first measured light intensity profile by measuring, from a first perspective relative to a photodetector device, photons that (i) originate from the light-emitting source in the subject, (ii) travel through turbid biological tissue of the subject, and (iii) are emitted from a first surface region of the subject;
   fitting the first measured light intensity profile with a parameter-based biophotonic function to obtain an initial determination of the location and light intensity of the light-emitting source;
   determining the depth of the light-emitting source, comprising:
      (a) measuring light emission intensity from the subject at two or more different wavelengths between about 400 and about 1000 nm;
      (b) obtaining information related to optical properties of the subject's tissue;
      (c) using the measured light intensities and the obtained information to determine the depth of the light-emitting source; and
      (d) refining one or more parameters of the biophotonic function to obtain the depth and light intensity of the light-emitting source.

13. The method of claim 12, wherein (a) is carried out by measuring light intensities at each at two different wavelengths, (b) includes measuring the coefficients of attenuation and diffusion in tissue or material corresponding to that of the subject, and (c) includes using said coefficients in a formula to estimate depth of said source.

14. The method of claim 13, wherein (b) is carried out by determining, at two or more different wavelengths, light intensities from by a light-emitting source located at each of a plurality of depths in tissue or material corresponding to that of the subject, and (c) is carried out by matching the measured light intensities with reference light intensities determined at each of the plurality of depths.

15. The method of claim 14, wherein (a) includes measuring a spectral profile of light intensities from the light-emitting source, (b) is carried out by determining spectral profiles of light intensities from a light-emitting source at each of a plurality of depths, and (c) is carried out by matching the measured profile with the determined profiles, to identify a best curve fit.

16. The method of claim 12, wherein (b) is carried out by determining, at two or more different wavelengths, light intensities from by a light-emitting source located at each of a plurality of depths in tissue or material corresponding to that of the subject, and (c) is carried out by matching the measured light intensities with the light intensities determined at each of the plurality of depths.

17. The method of claim 12, wherein (a) includes measuring a spectral profile of light intensities from the light-emitting source, (b) is carried out by determining spectral profiles of light intensities from a light-emitting source at each of a plurality of depths, and (c) is carried out by matching the measured profile with the determined profiles, to identify a best curve fit.

18. The method of claim 12 further comprising using the approximate depth and shape of the source in the subject and superimposing a three-dimensional visual representation onto an image of the subject.

19. The method of claim 12, wherein the subject is in a dark imaging chamber included in an enclosure that includes a door and a seal on the door, and the method further includes providing a light-tight seal to when the door is closed.

20. A non-transitory program storage device readable by a machine tangibly embodying a program of instructions executable by the machine to perform a method of investigating the location and size of a light-emitting source in a subject, wherein the method comprising:
   obtaining a first measured light intensity profile by measuring, from a first perspective relative to a photodetector device, photons that (i) originate from the light-emitting source in the subject, (ii) travel through turbid biological tissue of the subject, and (iii) are emitted from a first surface region of the subject;
   fitting the first measured light intensity profile with a parameter-based biophotonic function to obtain an initial determination of the location and light intensity of the light-emitting source; and
   refining one or more parameters of the biophotonic function to obtain an approximate depth and light intensity of the light-emitting source in the subject.

* * * * *